(12) United States Patent
Yang et al.

(10) Patent No.: US 10,463,873 B1
(45) Date of Patent: Nov. 5, 2019

(54) NON-INVASIVE PHOTOTHERAPEUTIC SYSTEM

(71) Applicant: JiPhoton Therapeutics Inc., Bedford, NY (US)

(72) Inventors: Chaohui Yang, Bedford, NY (US); Xicheng Yang, Shanghai (CN); Rui Wu, Guangdong (CN)

(*) Notice: Subject to any disclaimer, the term of this patent is extended or adjusted under 35 U.S.C. 154(b) by 0 days.

(21) Appl. No.: 15/977,209

(22) Filed: May 11, 2018

(51) Int. Cl.
*A61N 5/06* (2006.01)
*A61N 5/067* (2006.01)

(52) U.S. Cl.
CPC .... *A61N 5/0603* (2013.01); *A61N 2005/0606* (2013.01); *A61N 2005/067* (2013.01); *A61N 2005/0626* (2013.01); *A61N 2005/0628* (2013.01); *A61N 2005/0643* (2013.01); *A61N 2005/0651* (2013.01)

(58) Field of Classification Search
CPC .......... A61N 5/0603; A61N 2005/0606; A61N 2005/0643
USPC .......................................................... 607/89
See application file for complete search history.

(56) References Cited

U.S. PATENT DOCUMENTS

| | | | |
|---|---|---|---|
| 9,180,308 B1 * | 11/2015 | Frost ................ | A61N 5/0622 |
| 2006/0112962 A1 * | 6/2006 | Tebbutt ............. | A61M 16/06 |
| | | | 128/206.29 |
| 2011/0240040 A1 * | 10/2011 | Westbrook ......... | A61B 13/00 |
| | | | 128/860 |
| 2012/0214122 A1 * | 8/2012 | Dwyer ............... | A61C 19/066 |
| | | | 433/29 |
| 2013/0280671 A1 * | 10/2013 | Brawn ............... | A61N 5/0603 |
| | | | 433/24 |
| 2014/0190489 A1 * | 7/2014 | Chen ................. | A61F 5/566 |
| | | | 128/848 |
| 2015/0164682 A1 * | 6/2015 | Remmers .......... | A61B 5/4812 |
| | | | 600/301 |
| 2017/0173353 A1 * | 6/2017 | Demarest .......... | A61C 19/063 |
| 2019/0076227 A1 * | 3/2019 | Charkhandeh ..... | A61C 19/05 |
| 2019/0159877 A1 * | 5/2019 | Sanders ............. | A61C 19/066 |

FOREIGN PATENT DOCUMENTS

WO WO 2017044931 A1 * 3/2017 .......... A61N 5/0603

* cited by examiner

*Primary Examiner* — Gary Jackson
*Assistant Examiner* — Zahed Kabir
(74) *Attorney, Agent, or Firm* — Rui Wu

(57) ABSTRACT

A phototherapeutic system for providing phototherapy inside a user's mouth comprises a housing; and a plurality of radiation sources disposed in the housing, wherein the plurality of radiation sources is configured to provide to the user's mouth a plurality of beams, wherein at least two beams of the plurality of beams have different wavelengths, and wherein a portion of the housing is configured to receive a pressure resulting from the user's mouth so as to prevent the housing from moving during the phototherapy.

20 Claims, 18 Drawing Sheets

NON-INVASIVE PHOTOTHERAPEUTIC SYSTEM

BACKGROUND

1. Technical Field

The present disclosure relates generally to non-invasive phototherapeutic system and method of providing intra-oral phototherapy.

2. Discussion of Technical Background

It has been discovered that intra-oral phototherapy is an effective treatment for improving a patient's health condition. In an intra-oral phototherapy, electromagnetic radiations in form of radiation beams are provided inside the patient's mouth. Configurations of the existing phototherapeutic systems, however, limit the applicability for such intra-oral phototherapy. For example, a patient needs to use his hand to hold the phototherapeutic system during the whole treatment, which adversely affects the patient's user experience. Alternatively, an external device may be used to replace the patient's hand to hold the phototherapeutic system during the whole treatment, which however limits the portability of the phototherapeutic system since the phototherapeutic system has to be close to the external device when in use. In addition, the electromagnetic radiations provided by the existing phototherapeutic system are limited to either continuous or pulsed laser beams. The limited waveforms of the electromagnetic radiations accordingly provide a very limited number of forms of stimulations to the patient, which adversely affect the effectiveness of the phototherapy particularly after using the phototherapeutic system for several times. Therefore, a need exists for an improved phototherapeutic system and method for providing the intra-oral phototherapy.

SUMMARY

In an example embodiment, there is provided a phototherapeutic system for providing phototherapy inside a user's mouth, comprising: a housing; and a plurality of radiation sources disposed in the housing, wherein the plurality of radiation sources is configured to provide to the user's mouth a plurality of beams, wherein at least two beams of the plurality of beams have different wavelengths, and wherein a portion of the housing is configured to receive a pressure resulting from the user's mouth so as to prevent the housing from moving during the phototherapy.

In another example embodiment, there is provided a method of providing phototherapy inside a user's mouth, comprising: providing a phototherapeutic system, comprising: a housing; a plurality of radiation sources disposed in the housing, wherein the plurality of radiation sources is configured to provide to the user's mouth a plurality of beams, wherein at least two beams of the plurality of beams have different wavelengths, wherein a portion of the housing is configured to receive a pressure resulting from the user's mouth so as to prevent the housing from moving during the phototherapy; one or more sensors disposed in the housing, wherein the one or more sensors are configured to provide one or more values related to surrounding of the one or more sensors; a user interface disposed on an exterior surface of the housing, wherein the user interface is configured to receive an input for controlling operation of the phototherapeutic system; a switch control circuit disposed in the housing; and one or more output components disposed in the housing; controlling, by the switch control circuit, an operating state of the phototherapeutic system based on the input received by the user interface and the one or more values provided by the one or more sensors; and delivering, by the one or more output components, to the user information related to the operating state of the phototherapeutic system.

Other concepts relate to software for operating the phototherapeutic system as described herein. A software product, in accord with this concept, includes at least one machine-readable non-transitory medium and information carried by the medium.

In an example embodiment, there is provided a machine-readable tangible and non-transitory medium having instructions for providing phototherapy inside a user's mouth through a phototherapeutic system, the phototherapeutic system comprising: a housing; a plurality of radiation sources disposed in the housing, wherein the plurality of radiation sources is configured to provide to the user's mouth a plurality of beams, wherein at least two beams of the plurality of beams have different wavelengths, wherein a portion of the housing is configured to receive a pressure resulting from the user's mouth so as to prevent the housing from moving during the phototherapy; one or more sensors disposed in the housing, wherein the one or more sensors are configured to provide one or more values related to surrounding of the one or more sensors; a user interface disposed on an exterior surface of the housing, wherein the user interface is configured to receive an input for controlling operation of the phototherapeutic system; a switch control circuit disposed in the housing; and one or more output components disposed in the housing, wherein the instructions, when read by a hardware processor system, causes the hardware processor system to: control, through the switch control circuit, an operating state of the phototherapeutic system based on the input received by the user interface and the one or more values provided by the one or more sensors; and deliver, through the one or more output components, to the user information related to the operating state of the phototherapeutic system.

BRIEF DESCRIPTION OF THE DRAWINGS

The embodiments will be more readily understood in view of the following description when accompanied by the below figures and wherein like reference numerals represent like elements, wherein.

DETAILED DESCRIPTION

Figure 1:
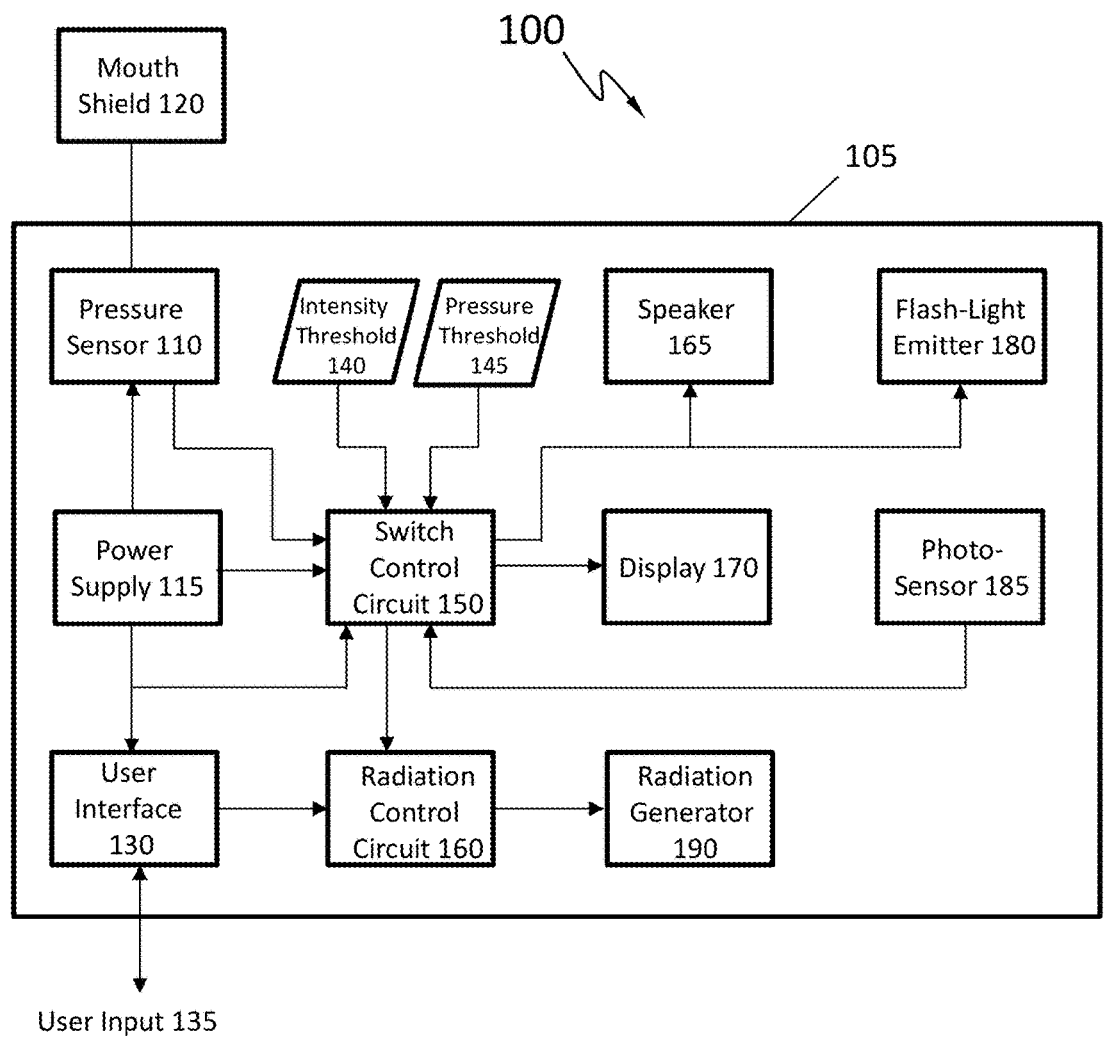
FIG. 1 is a schematic diagram of a phototherapeutic system for providing phototherapy inside a user's mouth according to an embodiment of the present disclosure.

Reference will now be made in detail to the embodiments of the present disclosure, examples of which are illustrated in the accompanying drawings. While the present disclosure will be described in conjunction with the embodiments, it will be understood that they are not intended to limit the present disclosure to these embodiments. On the contrary, the present disclosure is intended to cover alternatives, modifications, and equivalents, which may be included within the spirit and scope of the present disclosure as defined by the appended claims.

In addition, in the following detailed description of embodiments of the present disclosure, numerous specific details are set forth in order to provide a thorough understanding of the present disclosure. However, it will be recognized by one of ordinary skill in the art that the present disclosure may be practiced without these specific details. In other instances, well-known methods, procedures, components, and circuits have not been described in detail as not to unnecessarily obscure aspects of the embodiments of the present disclosure.

Described herein are phototherapeutic system and method of providing phototherapy inside a user's mouth. The phototherapeutic system includes a radiation generator having a plurality of radiation sources. The plurality of radiation sources may be arranged in a row, in a column, in a two-dimensional array, in a three-dimensional array, or in any other suitable manners. In an embodiment, at least one of the radiation sources can be rotatable at their respective locations so that the radiation beams provided by the at least one of the radiation sources can be redirected to different directions at different times, thereby scanning over a predetermined portion inside the user's mouth. In addition, the radiation beams provided by adjacent radiation sources may be partially overlapped. The radiation beams provided by different radiation sources may have different wavelengths and different powers. Further, the phototherapeutic system may include a radiation control circuit configured to modulate the radiation beams to different waveforms according to one or more parameters selected from a group consisting of average power, crest power, trough power, wave frequency, wave shape, and operating time period.

In an embodiment, the phototherapeutic system includes a housing, a portion of which receives a pressure directly or indirectly from the user's mouth during the phototherapy. The pressure prevents the housing from moving during the phototherapy. In an embodiment, the portion of the housing includes a track. The track may be made from any suitable material, for example, plastic. In an embodiment, the track is a saw-tooth shaped track. In some examples, the user's mouth may apply the pressure on the portion of the housing by biting between adjacent teeth of the track. In some examples, a mouth shield may be mounted on the housing through the track. In addition, the mouth shield may slide along the housing through the track so as to adjust relative positions of the plurality of radiation sources with respect to the user's mouth. As such, the user's mouth may apply the pressure on the portion of the housing by biting the mouth shield. In an embodiment, the track may have any other suitable configurations. For example, the track may include a plurality of columns arranged in a two-dimensional array or any other suitable patterns. In this example, the user's mouth may apply the pressure on the portion of the housing by biting between adjacent columns of the track.

In an embodiment, the phototherapeutic system includes a variety of sensors disposed in or on an exterior surface of the housing and configured to collect data surrounding the phototherapeutic system. Examples of the variety of sensors may include, but are not limited to, a temperature sensor, a photo-sensor, and a distance sensor. The phototherapeutic system may further include a switch control circuit configured to control an operating state of the phototherapeutic system based on the user input and the data collected by the variety of sensors. The use of the switch control circuit may prevent the phototherapeutic system from being accidentally turned on by the user. For example, in response to the user's request to turn on the phototherapeutic system, the switch control circuit may compare the data in forms of one or more values collected and provided by the variety of sensors with a plurality of one or more respective thresholds. As a result, the switch control circuit may change the operating state of the phototherapeutic system from a stop state to an active state by controlling the radiation sources to provide the radiation beams when the one or more values all meet or cross the one or more respective thresholds. Otherwise, the switch control circuit may deliver, through one or more output components, for example, a speaker, a display, a flash-light emitter, or any combination therefore, to the user the information indicative of denying the user's request to turn on the phototherapeutic system when not all of the one or more values meet or cross the one or more respective thresholds. In some examples, the switch control circuit may change the operating state of the phototherapeutic system from the active state to the stop state by controlling the radiation sources to stop providing the radiation beams when all the one or more values do not meet or cross the one or more respective thresholds. In some examples, the switch control circuit may be separate from the radiation control circuit. In some examples, the switch control circuit and the radiation control circuit may be combined into a single control circuit.

Referring to FIG. 1, a schematic diagram of a phototherapeutic system 100 is illustrated. The phototherapeutic system 100 may be a stand-alone system for providing the phototherapy inside a user's mouth. As shown, the phototherapeutic system 100 includes a housing 105 and a mouth shield 120 mounted on the housing 105. The housing 105 may be made from any suitable material, such as cleanable Acrylonitrile Butadiene Styrene (ABS)/polycarbonate plastic. The phototherapeutic system 100 further includes various components disposed in or on the exterior surface of the housing 105. The various components of the phototherapeutic system 100 may be arranged as shown or in any other suitable manners.

As shown, the phototherapeutic system 100 includes a radiation generator 190. The radiation generator 190 may be configured to provide a plurality of radiation beams in the user's mouth for use during the phototherapy. The radiation generator 190 may include a plurality of radiation sources each configured to emit a radiation beam. For example, each of the radiation beams may have a power between 5 milliwatts (mW) and 20 mW. The radiation sources may be laser diodes (LDs), light-emitting diodes (LEDs), vertical external cavity surface-emitting lasers (VECSELs), vertical cavity surface-emitting lasers (VCSELs), or any combination thereof. The radiation sources may be arranged in a row or a column. Alternatively, the radiation sources may be arranged in a two-dimensional array or a three-dimensional array. In addition, the radiation beams provided by different radiation sources may have different wavelengths and different powers. For example, some radiation sources may provide first radiation beams having a wavelength or wavelengths between 500 nanometer (nm) and 700 nm, while other radiation sources provide second radiation beams having a wavelength or wavelengths between 700 nm and 900 nm. For another example, some radiation sources may provide the first radiation beams having a wavelength or wavelengths between 630 nm and 650 nm, while the other radiation sources provide the second radiation beams having a wavelength or wavelengths between 690 nm and 705 nm. For yet another example, some radiation sources may provide the first radiation beams having a wavelength or wavelengths between 630 nm and 650 nm, while the other radiation sources provide the second radiation beams having a wavelength or wavelengths between 810 nm and 830 nm. Further, the radiation beams provided by adjacent radiation sources may be partially overlapped. In an embodiment, the radiation generator 190 is a static radiation generator. In a static radiation generator, none of the radiation sources can be rotatable at their respective locations. Accordingly, directions of the radiation beams provided by the radiation sources are fixed during the operation of the phototherapeutic system 100. In an embodiment, the radiation generator 190 is a dynamic radiation generator. In a dynamic radiation generator, at least one of the radiation sources can be rotatable at its respective location so that the radiation beams provided by the at least one of the radiation sources can be redirected to different directions at different times, thereby scanning over a predetermined portion inside the user's mouth. More details regarding the radiation generator 190 will be discussed below with respect to FIGS. 2, 3, 4A, and 4B.

The phototherapeutic system 100 includes a user interface 130. The user interface 130 may be configured to receive a user input 135 from the user of the phototherapeutic system 100. The user input 135 may include a request to turn on the phototherapeutic system 100 for starting the phototherapy. The user input 135 may include a request to turn off the phototherapeutic system 100 for stopping the phototherapy. In addition, the user input 135 may be in connection of one or more parameters related to waveforms of the radiation beams provided by one or more radiation sources of the radiation generator 190. In some examples, the user input 135 may explicitly indicate values for one or more parameters selecting from a group consisting of average power, crest power, trough power, wave frequency, wave shape, and operating time period. In some examples, the user input 135 may indicate the user's personal information which may be further used, by a radiation control circuit 160, to determine the one or more parameters as described above using, e.g., machine learning algorithms.

As shown, the radiation control circuit 160 includes an input port coupled to the user interface 130 and configured to receive the user input 135. The radiation control circuit 160 further includes an output port coupled to the radiation generator 190. The radiation control circuit 160 may be configured to provide to the radiation generator 190 a control signal to modulate the radiation beams provided by the radiation generator 190 to desirable waveforms according to the one or more parameters selected from the group consisting of average power, crest power, trough power, wave frequency, wave shape, and operating time period based on the user input 135. In some examples, the radiation control circuit 160 may be further configured to determine the appropriate one or more parameters related to the radiation beams based on the user's personal information included in the user input 135 as discussed above.

In an embodiment, a portion of the housing 105 receives a pressure directly or indirectly from the user's mouth during the phototherapy. The pressure prevents the housing 105 from moving before or during the phototherapy. In an embodiment, the portion of the housing 105 includes a track. The track may be made from any suitable material, for example, plastic. In an embodiment, the track is a saw-tooth shaped track. In some examples, the user's mouth may apply the pressure on the portion of the housing 105 by biting between adjacent teeth of the track. In some examples, the mouth shield 120 may be mounted on the housing 105 through the track. In addition, the mouth shield 120 may slide along the housing 105 through the track so as to adjust relative positions of the plurality of radiation sources in the radiation generator 190 with respect to the user's mouth. As such, the user's mouth may apply the pressure on the portion of the housing 105 by biting the mouth shield 120, which may assist keeping the user's mouth wide open while maintaining the position of the phototherapeutic system 100 during the phototherapy, thus preventing the phototherapeutic system 100 from slipping into, or being swallowed by the user into the user's digestive canal. In an embodiment, the track may have any other suitable configurations. For example, the track may include a plurality of columns arranged in a two-dimensional array or any other suitable patterns. In this example, the user's mouth may apply the pressure on the portion of the housing by biting between adjacent columns of the track.

In an embodiment, the phototherapeutic system 100 includes one or more sensors disposed in or on the exterior surface of the housing 105 and configured to collect data surrounding the phototherapeutic system 100. The phototherapeutic system 100 may further include a switch control circuit 150 configured to control an operating state of the phototherapeutic system 100 based on the user input 135 and the data collected by the one or more sensors. In some examples, the switch control circuit 150 may be separate from the radiation control circuit 160 as shown in FIG. 1. In some examples, the switch control circuit 150 and the radiation control circuit 160 may be combined into a single control circuit. Examples of the one or more sensors may include a photo-sensor 185 and a pressure sensor 110 as shown in FIG. 1. The photo-sensor 185 may have an output port coupled to the switch control circuit 150. The photo-sensor 185 may be configured to determine a total intensity related to radiations received by the photo-sensor 185 from surroundings of the photo-sensor 185. The photo-sensor 185 may be further configured to provide the total intensity to the switch control circuit 150. The pressure sensor 110 may have an output port coupled to the switch control circuit 150. The pressure sensor 110 may be attached to the portion of the housing 105 as described above. The pressure sensor 110 may be configured to determine the pressure applied to the portion of the housing 105 and further provide the pressure value to the switch control circuit 150. In addition or alternatively, examples of the one or more sensors may further include, but are not limited to, a distance sensor and/or a temperature sensor. The distance sensor may have an output port coupled to the switch control circuit 150. The distance sensor may be configured to determine a temperature around the phototherapeutic system 100 and further provide the temperature to the switch control circuit 150. The distance sensor may have an output port coupled to the switch control circuit 150. The distance sensor may be situated in or around the radiation generator 190. The distance sensor may be configured to determine a distance between the radiation generator 190 and a specific part, for example, the tongue root or the uvulae, inside the user's mouth with aid of ultrasounds, infrared rays, and/or other suitable means.

In an embodiment, the use of the switch control circuit 150 may prevent the phototherapeutic system 100 from being accidentally turned on by the user. For example, in response to the user's request (included in the user input 135) to turn on the phototherapeutic system 100, the switch control circuit 150 may compare the data in forms of one or more values collected and provided by the one or more sensors (e.g., the photo-sensor 185 and the pressure sensor 110) with a plurality of one or more respective thresholds. As a result, the switch control circuit 150 may change the operating state of the phototherapeutic system 100 from a stop state to an active state by controlling the radiation sources of the radiation generator 190 to provide the radiation beams when the one or more values all meet or cross the one or more respective thresholds. In the example as shown in FIG. 1, the phototherapeutic system 100 includes the photo-sensor 185 and the pressure sensor 110. The switch control circuit 150 may compare the total intensity of radiations determined by the photo-sensor 185 with an intensity threshold 140. The switch control circuit 150 may further compare the pressure value determined and provided by the pressure sensor 110 with a pressure threshold 145. The switch control circuit 150 may change the operating state of the phototherapeutic system 100 from the stop state to the active state by controlling the radiation sources of the radiation generator 190 to provide the radiation beams when the total intensity provided meets or crosses the intensity threshold 140, and the pressure value meets or crosses the pressure threshold 145. In addition, the switch control circuit 150 may further control one or more output components to deliver to the user information related to the operating state change of the phototherapeutic system 100. The one or more output components may include, but are not limited to a display 170, a speaker 165, a flash-light emitter 180, or any combination thereof.

The switch control circuit 150 may not be configured to change the operating state of the phototherapeutic system 100 from the stop state to the active state when not all of the one or more values provided by the one or more sensors meet or cross the one or more respective threshold. For example, the switch control circuit 150, although receipt through the user interface 130 of the user input 135 indicative of requesting to turn on the phototherapeutic system 100 or start the phototherapy, may not control the radiation generator 190 to provide the radiation beams when the total intensity of radiations determined by the photo-sensor 185 does not meet or cross the intensity threshold 140, and/or the pressure value determined by the pressure sensor 110 does not meet or cross the intensity threshold 145. In addition, the switch control circuit 150 may be further configured to control the one or more output components to deliver to the user information indicative of denying the user's request to operate the phototherapeutic system 100. As described above, the one or more output components, coupled to the switch control circuit 150, may include, but are not limited to, the speaker 165, the display 170, the flash-light emitter 180, or any combination thereof. Specifically, the speaker 165 may output a recorded voice message, a beep, or any other suitable sound. The flash-light emitter 180 may emit flash lights for a specific period of time, for example, a few seconds. The display 170 may display a text message indicating the user's request to start the phototherapy is denied.

In some examples, the switch control circuit 150 may change the operating state of the phototherapeutic system 100 from the active state to the stop state by controlling the radiation sources of the radiation generator 190 to stop providing the radiation beams when all the one or more values do not meet or cross the one or more respective thresholds during or after operating the phototherapeutic system 100. This may happen when the user intentionally or accidentally stops applying the pressure on the track attached on the housing 105 with or without aid of the mouth shield 120 in situations like stopping biting the mouth shield 120 and/or taking the phototherapeutic system 100 out of the user's mouth during the phototherapy. For example, the switch control circuit 150 may change the operating state of the phototherapeutic system 100 from the active state to the stop state during or after the phototherapy when the total intensity determined by the photo-sensor 185 fails to meet or cross the intensity threshold 140, and/or the pressure value determined by the pressure sensor 110 fails to meet or cross the pressure threshold 145. In the stop state, none of the radiation sources in the radiation generator 190 provides radiation beams.

The phototherapeutic system 100 may further include a power supply 115. The power supply 115 is any source of power, such as an AC power supply or a DC power supply, e.g., batteries, solar cells, etc. In an embodiment, the power supply 115 is an internal rechargeable Li-ion coin cell battery. A terminal (not shown) may be provided on the housing 105 for connecting a battery recharger (not shown) to the batteries in the housing 105. In some examples, the time needed to recharge the battery for one hour of use from a drained state is not greater than one hour.

Figure 2:
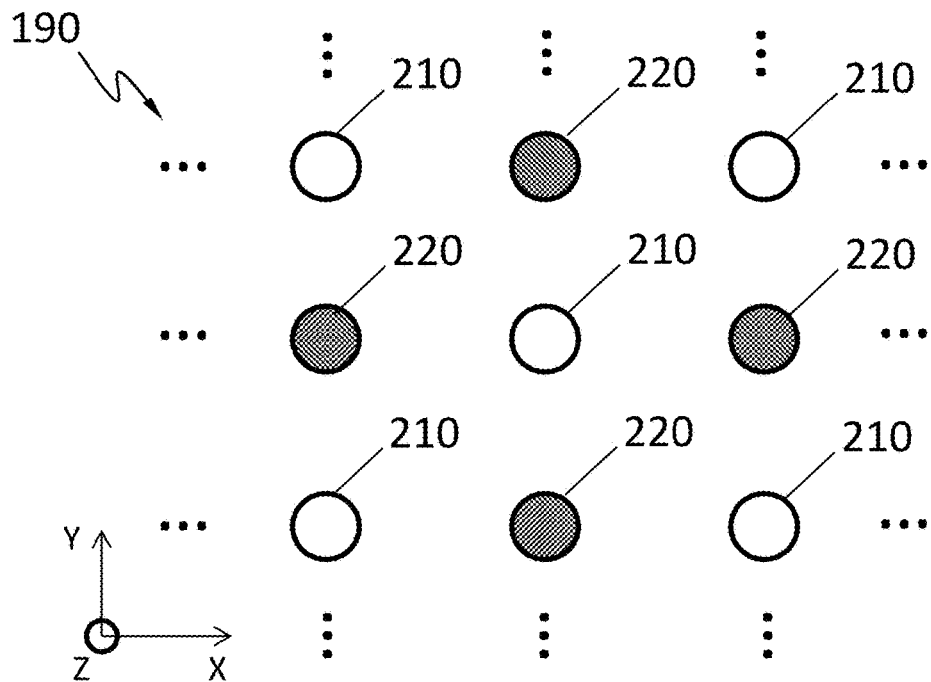
FIG. 2 is a perspective view of a radiation generator in an X-Y plane according to an embodiment of the present disclosure.

Referring to FIG. 2, a perspective view of the radiation generator 190 in an X-Y plane is shown according to an embodiment of the present disclosure. As shown, the radiation generator 190 includes a plurality of radiation sources 210, 220. In an embodiment, the plurality of radiation sources 210, 220 may provide radiation beams with different wavelengths. As shown, the radiation generator 190 may include a first kind of radiation sources, denoted by hollow circle, each provide radiation beams with a first wavelength. In an embodiment, the first wavelength may be between 500 nanometers (nm) and 700 nm. In an embodiment, the first wavelength may be between 630 nm and 650 nm. The radiation generator 190 may further include a second kind of radiation sources, denoted by solid circle, each provide radiation beams with a second wavelength. In an embodiment, the second wavelength may be between 700 nm and 900 nm. In an embodiment, the second wavelength may be between 690 nm and 705 nm. In some other examples, the plurality of radiation sources is the same kind of radiation sources providing radiation beams with the same wavelengths. In some other examples, the radiation generator 190 may provide radiation beams having three or more different wavelengths. Accordingly, the radiation generator 190 may include three or more different kinds of radiation sources, each provide radiation beams with one of the three or more wavelengths. Further, the plurality of radiation sources 210, 220 may be arranged alternately in a two-dimensional array in FIG. 2. In an embodiment, the plurality of radiation sources 210, 220 may be arranged in a two-dimensional array in some other suitable manner. In an embodiment, the plurality of radiation sources 210, 220 may be arranged in a column or in a row. In an embodiment, the plurality of radiation sources 210, 220 may be arranged in a three-dimensional array, where there may be a non-zero displacement in the Z direction between at least a pair of radiation sources 210, 220.

In an embodiment, the radiation generator 190 is a static radiation generator. This means none of the radiation sources (e.g., the radiation sources 210, 220) in the radiation generator 190 may be rotatable. As such, none of the radiation beams provided by the radiation sources (e.g., the radiation sources 210, 220) may change directions during operations.

Figure 3:
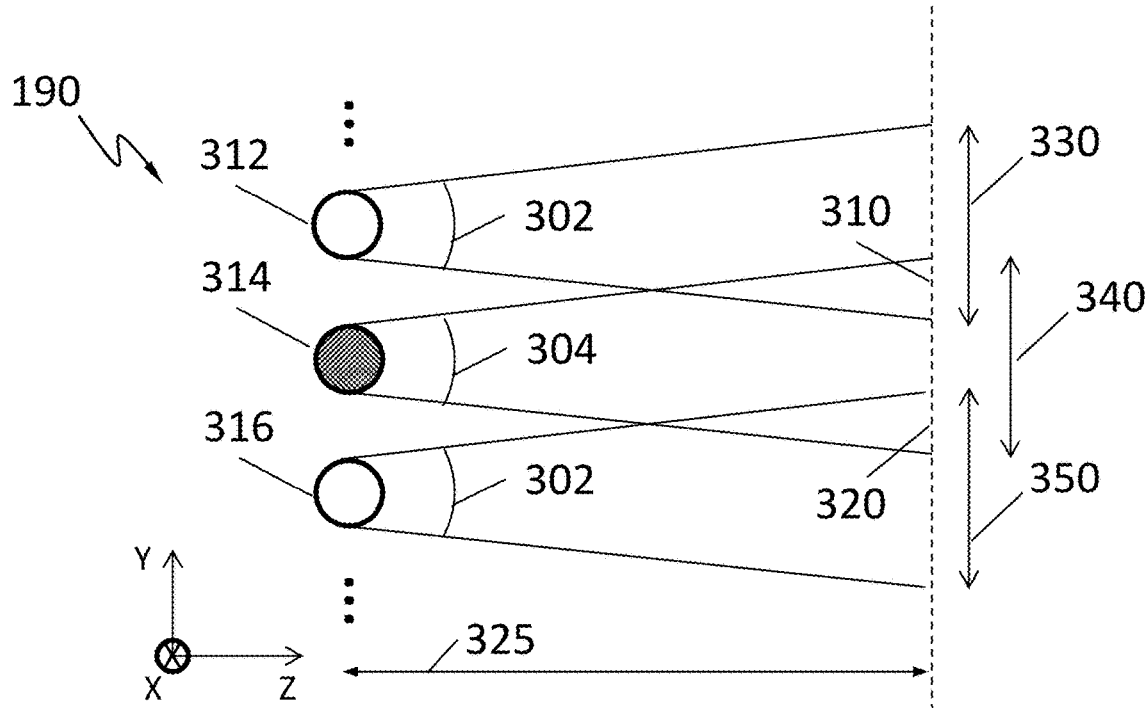
FIG. 3 is a side view showing operation of a static radiation generator in a Y-Z plane according to an embodiment of the present disclosure.

Referring to FIG. 3, a side view of the radiation generator 190 in a Y-Z plane is shown according to an embodiment of the present disclosure. As shown, the radiation generator 190 includes a first radiation source 312, a second radiation source 314, and a third radiation source 316. The first radiation source 312 and the third radiation source 316 are the first kind of radiation sources 210, as the second radiation source 314 is the second kind of radiation source 220. In this example, the radiation generator 190 is the static radiation generator. Accordingly, the radiation beams provided by the radiation sources 312, 314, 316 of the radiation generator 190 have the same direction during operations.

Further, as shown in this example, the radiation sources 312, 314, 316 are aligned in the X-Y plane, showing no displacement in the Z direction between any pair of the radiation sources 312, 314, 316. In some other examples, there may be a non-zero displacement in the Z direction between at least a pair of the radiation sources 312, 314, 316, resulting the plurality of radiation sources 312, 314, 316 arranged in a three-dimensional array. During operation, as shown in FIG. 3, a first radiation beam provided by the first radiation source 312 has a first beam angle 302 between 25 degrees and 30 degrees, with a first projection 330 of illuminations having a diameter between 2 centimeters (cm) and 5 cm at a distance 325 between 2 cm and 3.5 cm from the first radiation source 312. A second radiation beam provided by the second radiation source 314 has a second beam angle 304 between 25 degrees and 30 degrees, with a second projection 340 of illuminations having a diameter between 2 cm and 5 cm at the distance 325 from the second radiation source 314. A third radiation beam provided by the third radiation source 316 has the first beam angle 302, with a third projection 350 of illuminations having a diameter between 2 cm and 5 cm at the distance 325 from the third radiation source 316. A first overlapped portion 310 between the first projection 330 of illuminations and the second projection 340 of illuminations has a diameter between 1 cm and 3.5 cm, as a second overlapped portion 320 between the second projection 340 of illuminations and the third projection 350 of illuminations has a diameter between 1 cm and 3.5 cm. The first projection 330 of illuminations, the second projection 340 of illuminations, and the third projection 350 of illuminations are provided at the same time.

In an embodiment, the radiation generator 190 is a dynamic radiation generator. This means, at least one of the radiation sources (e.g., the radiation sources 210, 220) in the radiation generator 190 in FIG. 2 can be rotatable at its respective location so that the radiation beams provided by the at least one of the radiation sources (e.g., the radiation sources 210, 220) can be redirected to different directions at different times, thereby scanning over a predetermined portion inside the user's mouth.

Figure 4A:
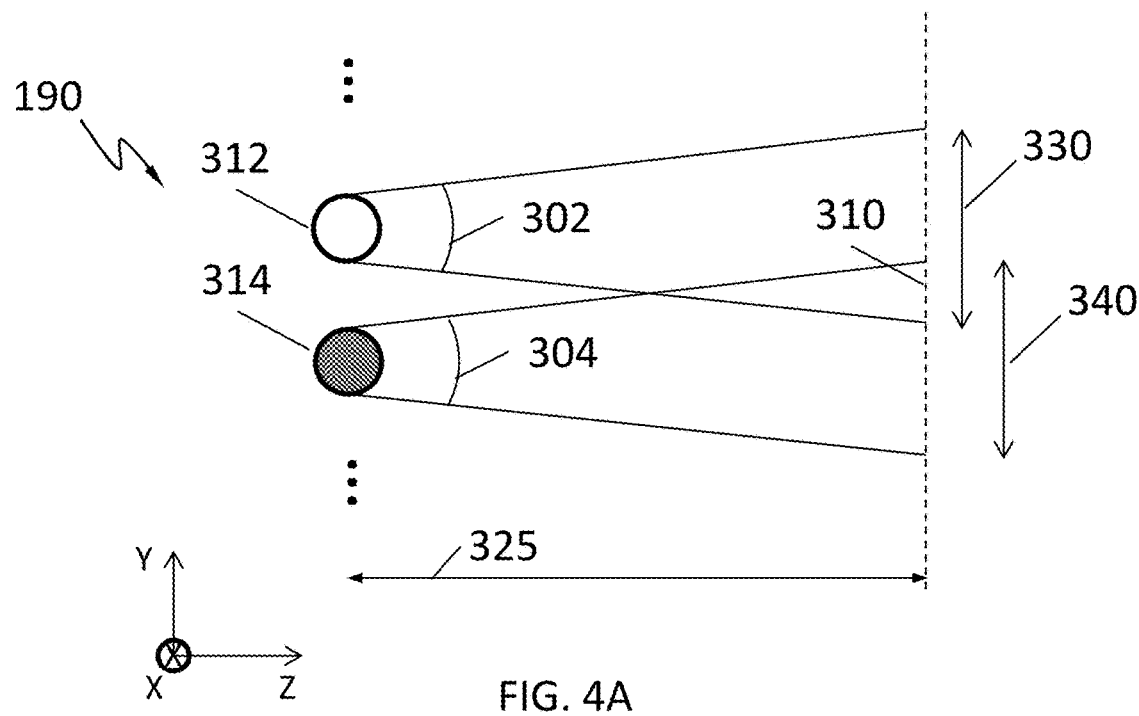
FIG. 4A is a side view showing operation of a dynamic radiation generator in a Y-Z plane at a first time according to an embodiment of the present disclosure.

Referring to FIG. 4A, a side view of the radiation generator 190 in the Y-Z plane during operation at a first time is shown according to an embodiment of the present disclosure. The radiation generator 190 includes the first radiation source 312 (denoted by the hollow circle) and the second radiation source 314 (denoted by the solid circle). The first radiation source 312 is the first kind of radiation source 210, and the second radiation source 314 is the second kind of radiation source 220. In this example, the radiation generator 190 is a dynamic radiation generator. Specifically, in this example the first radiation source 312 may be rotatable at its respective location so that the direction of the first radiation beams provided by the first radiation source 312 can be different at different times, as the second radiation source 314 cannot be rotatable and the direction of the second radiation beams provided by the second radiation source 314 is fixed. As shown in FIG. 4A, the first radiation beams provided by the first radiation source 312 has the first beam angle 302 between 25 degrees and 30 degrees, with the first projection 330 of illuminations having a diameter between 2 cm and 5 cm at the distance 325 between 2 cm and 3.5 cm from the first radiation source 312. Further, the second radiation beams provided by the second radiation source 314 has the second beam angle 304 between 25 degrees and 30 degrees, with the second projection 340 of illuminations having a diameter between 2 cm and 5 cm at the distance 325 between 2 cm and 3.5 cm from the second radiation source 312. As shown in FIG. 4A, the third projection 350 of illuminations as discussed with respect to FIG. 3 is not provided at the first time when both the first projection 330 of illuminations and the second projection 340 of illuminations are provided. In addition, a first portion (i.e., the lower portion as shown in FIG. 4A) of the first radiation beams provided by the first radiation source 312 is overlapped with the second radiation beams provided by the second radiation source 314 at the distance 325, as a second portion (i.e., the upper portion as shown in FIG. 4A) of the first radiation beams does not overlapped with the second radiation beams at the first time. Accordingly, the overlapped portion 310 of the first projection 330 of illuminations and the second projection 340 of illuminations has a diameter between 1 cm and 3.5 cm, similar to that as described with respect to FIG. 3.

Figure 4B:
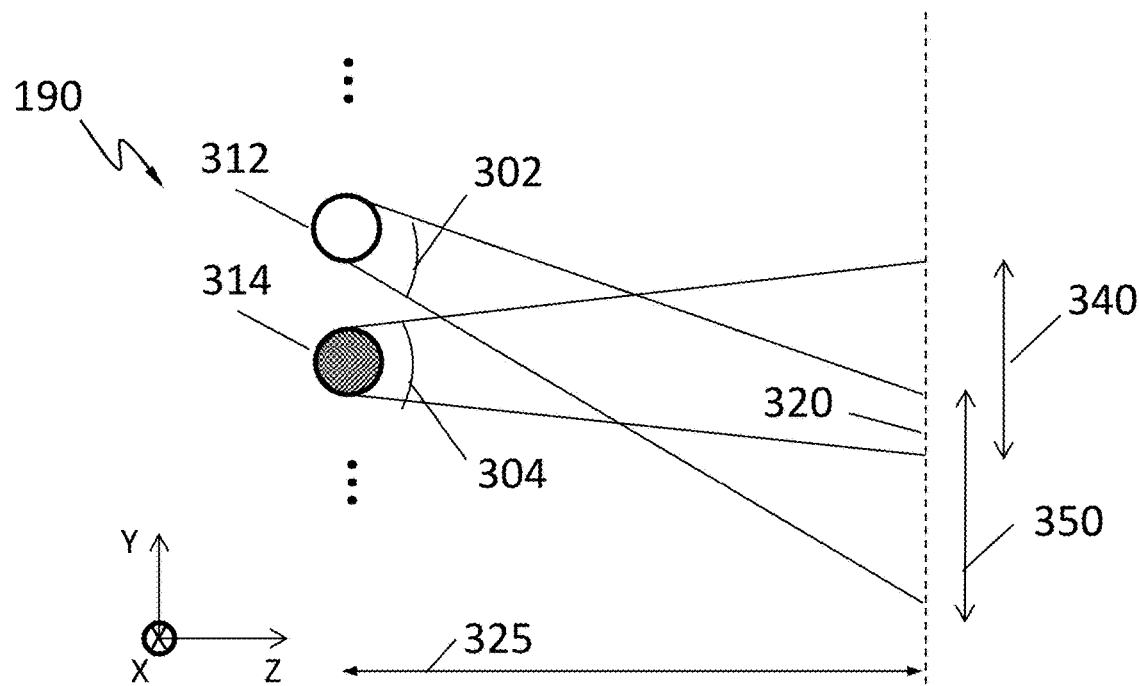
FIG. 4B is a side view showing operation of a dynamic radiation generator in a Y-Z plane at a second time according to an embodiment of the present disclosure.

Referring to FIG. 4B, the side view of the radiation generator 190 in the Y-Z plane during operation at a second time is shown according to an embodiment of the disclosure. At the second time, the first radiation source 302 rotates certain degrees so that the radiation beams provided by the first radiation source 302 is redirected, resulting in the third projection 350 of illuminations provided at the distance 325 from the first radiation source 302 at the second time. As shown, the second portion (i.e., the upper portion as shown in FIG. 4B) of the first radiation beams provided by the first radiation source 312 is overlapped with the second radiation beams provided by the second radiation source 314 at the distance 325 as the first portion (i.e., the lower portion as shown in FIG. 4B) of the first radiation beams does not overlap with the second radiation beams at the second time. The overlapped portion 320 of the second projection 340 of illuminations and the third projection 350 of illuminations has a diameter between 1 cm and 3.5 cm, similar to that described with respect to FIG. 3. As shown in FIG. 4B, the first projection 330 of illuminations is not provided at the first time when both the second projection 340 of illuminations and the third projection 350 of illuminations are provided. Together with FIG. 4A and FIG. 4B, it can be seen that the first projection 330 of illuminations, the second projection 340 of illuminations and the third projection 350 of illuminations may not be provided at the same time, which is different from FIG. 3. The minimal difference between the first time and the second time may sometimes be referred to as a transition period of the dynamic radiation generator. Further, the transition frequency of the dynamic radiation generator may be defined as the inverse of the transition period of the dynamic radiation generator.

Figure 5:
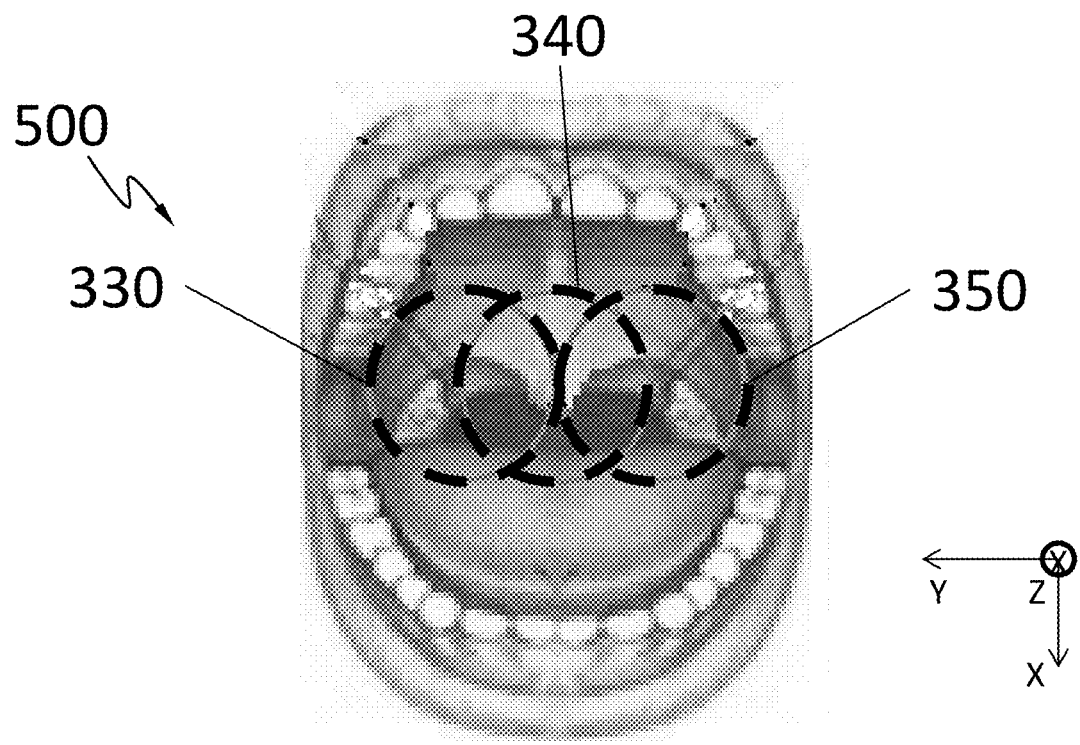
FIG. 5 is a perspective view of a user's mouth during phototherapy.

Referring to FIG. 5, a perspective view 500 of the user's mouth during phototherapy in the X-Y plane is shown. In this example, the radiation beams provided by the radiation generator (e.g., the radiation generator 190) may be illuminated onto the user's throat. Specifically, the first projection 330 of illuminations, the second projection 340 of illuminations, and the third projection 350 of illuminations cover a wide range of the user's throat, covering the uvula and the palatine tonsil.

Figure 6:
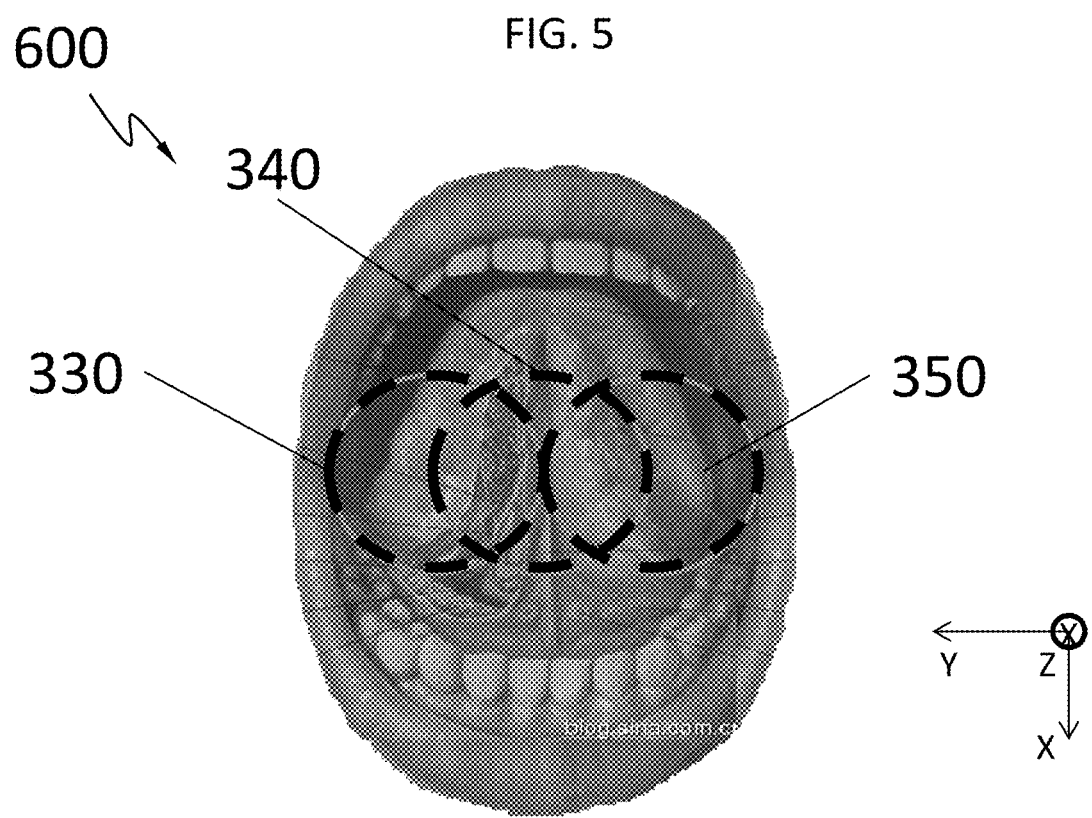
FIG. 6 is a perspective view of a user's mouth during phototherapy.

Referring to FIG. 6, another perspective view 600 of the user's mouth during phototherapy in the X-Y plane is shown. In this example, the radiation beams provided by the radiation generator (e.g., the radiation generator 190) may be illuminated onto the user's tongue. Specifically, the first projection 330 of illuminations, the second projection 340 of illuminations, and the third projection 350 of illuminations cover a wide range of the user's tongue root, for example, the user's root of tongue.

With respect to both FIG. 5 and FIG. 6, the first projection 330 of illuminations, the second projection 340 of illuminations, and the third projection 350 of illuminations may be provided at the same time when the radiation generator 190 is configured as the static radiation generator. In an embodiment, the first projection 330 of illuminations, the second projection 340 of illuminations, and the third projection 350 of illuminations may be provided at different times when the radiation generator 190 is configured as the dynamic radiation generator.

Figure 7:
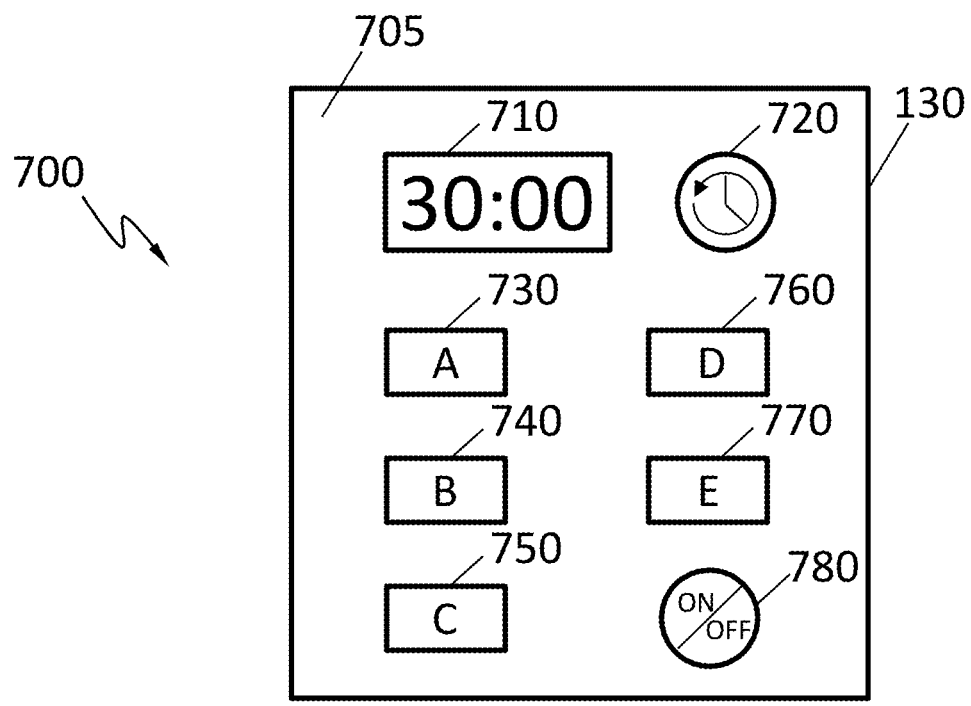
FIG. 7 is a perspective view of a user interface for use in a phototherapeutic system according to an embodiment of the disclosure.
Figure 8:
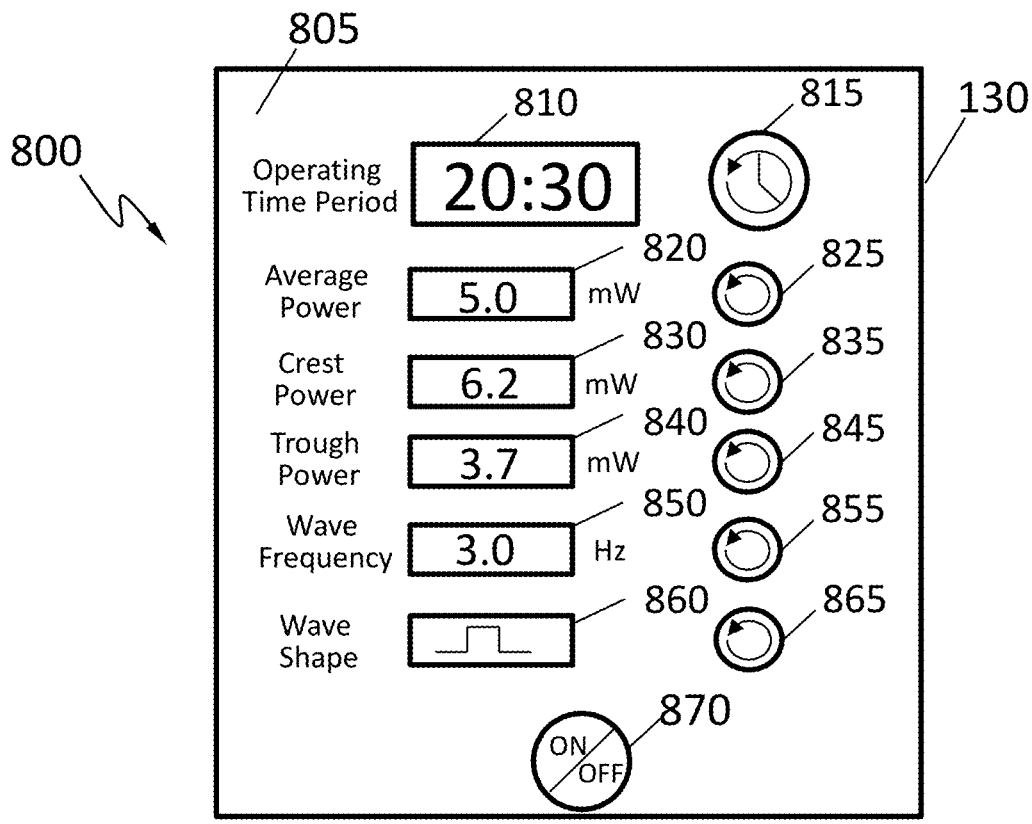
FIG. 8 is a perspective view of a user interface for use in a phototherapeutic system according to an embodiment of the disclosure.
Figure 9:
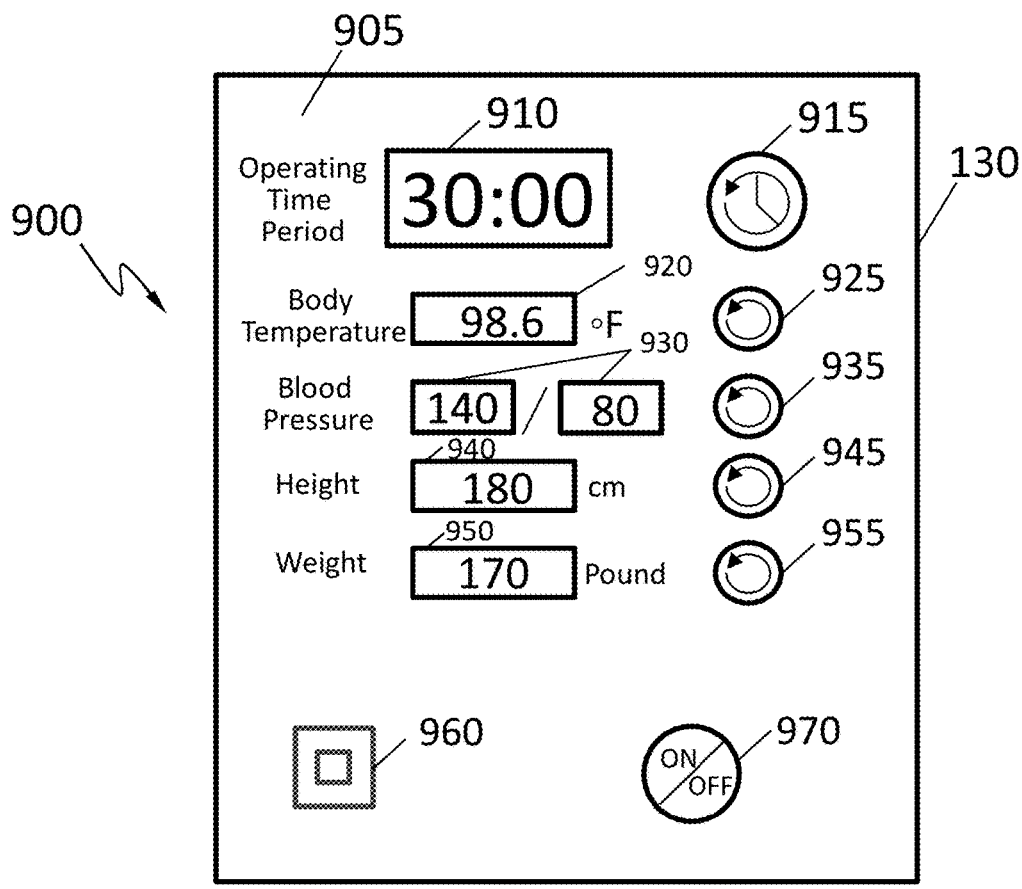
FIG. 9 is a perspective view of a user interface for use in a phototherapeutic system according to an embodiment of the disclosure.

FIGS. 7-9 shows three examples 700, 800, 900 of the user interface 130. These three examples shown in FIGS. 7-9 are merely for illustrating purposes and by no meaning limiting. As described above, the user interface 130 may be configured to receive the user input 135 and transmit the user input 135 to the radiation control circuit 160, which may be further configured to determine, based on the user input 135, one or more parameters used to modulate the waveforms of the radiation beams provided by the radiation generator 190. The three examples shown in FIGS. 7-9 illustrates using the user interface 130 for receiving different kinds of user input 135 related to the one or more parameters as discussed above.

Referring to FIG. 7, an exemplary perspective view 700 of the user interface 130 for use in the phototherapeutic system 100 is shown according to an embodiment of the disclosure. As shown, the user interface 130 includes a display window 710 configured to display the operating time period. In an embodiment, the initial value of the operating time period is 30 minutes by default. In an embodiment, the initial value of the operating time period may be set to any other suitable length of time. In an embodiment, the initial value of the operating time period will be shown with respect to a selection of the therapy mode by the user after one of the buttons 730-750 is depressed by the user as described below. The value of the operating time period shown in the display window 710 may decrease as time elapses after starting operating the phototherapeutic system (e.g., the phototherapeutic system 100). The value of the operating time period may be adjusted by the user through the button 720. For example, depressing the button 720 clockwise may increase the value of the operating time period as depressing the button 720 counterclockwise may decrease the value of the operating time period shown on the display window 710, or vice versa.

Buttons 730-770, denoted by alphabets "A" to "E," corresponds to different therapy modes. Each therapy mode corresponds to a specific but different set of values for the one or more parameters used to define the waveforms of the radiation beams provided by the radiation generator 190. The one or more parameters may include, but are not limited to, operating time period, average power, crest power, trough power, wave frequency, wave shape of the waveforms of the radiation beams provided by the radiation generator 190, or any combination thereof. As such, selecting a therapy mode by depressing one of the buttons 730-770 is equivalent to select a predetermined set of values for the one or more parameters.

The user interface 130 as shown in FIG. 7 further includes a button 780 used to communicate the user's request to turn on or off the phototherapeutic system (e.g., the phototherapeutic system 100). Specifically, depressing the button 780 by the user during the phototherapy may turn off the phototherapeutic system (e.g., the phototherapeutic system 100) though depressing the button 780 by the user when the phototherapeutic system (e.g., the phototherapeutic system 100) is not performing or operating may not necessarily turn on the phototherapeutic system as discussed above with respect to FIG. 1.

In an embodiment, the buttons 720-780 are manually actuatable elements provided on an exterior surface 705 of the user interface 130. In addition, the display window 710 is a backlit liquid crystal display (LCD) and the buttons 720-780, the display window 710, or both are recessed from the exterior surface 705 of the user interface 130 to prevent them from being accidentally or inadvertently actuated or damaged. The shape, texture, or both of each button 720-780 can be unique to that button to enable the user to identify a particular button by its feel. One or more of the buttons 720-780 or features on the buttons 720-780 can also be lighted, e.g., backlit, so that they can be seen in a dark room.

Alternatively, in an embodiment, the buttons 720-780 are virtually elements. In addition, both the buttons 720-780 and the display window 710 are presented on an LCD screen provided as the exterior surface 705 of the user interface 130. Further, the LCD screen is a backlit LCD so that one or more of the display window 710 and the buttons 720-780 can be lighted and seen in a dark room.

Referring to FIG. 8, another exemplary perspective view 800 of the user interface 130 for use in the phototherapeutic system 100 is shown according to another embodiment of the disclosure. As shown, the user interface 130 includes a plurality of indicators (e.g., in form of texts) of parameters related to the waveforms of radiation beams provided by the radiation generator (e.g., the radiation generator 190). The user interface 130 further includes a display window 810, 820, 830, 840, 850, 860, close to each of the indicators. The display windows 810, 820, 830, 840, 850, 860 are configured to display values, determined and inputted by the user, of the parameters identified by the corresponding indicators. The initial values related to the corresponding indicators may be provided as shown in FIG. 8 or may be set to any other suitable values. In an embodiment, the user interface 130 further includes a button 815, 825, 835, 845, 855, 865 near each of the display windows 810, 820, 830, 840, 850, 860. The buttons 815, 825, 835, 845, 855, 865 are configured to receive the user input (e.g., the user input 135) to adjust the values shown in the neighboring display windows 810, 820, 830, 840, 850, 860. In an embodiment, depressing the buttons 815, 825, 835, 845, 855, 865 clockwise may increase the value shown in the respective neighboring display windows 810, 820, 830, 840, 850, 860, as depressing the buttons 815, 825, 835, 845, 855, 865 counterclockwise may decrease the value shown in the respective neighboring display windows 810, 820, 830, 840, 850, 860, or vice versa.

The user interface 130 as shown in FIG. 8 further includes a button 870 used to communicate the user's request to turn on or off the phototherapeutic system (e.g., the phototherapeutic system 100). Specifically, depressing the button 870 by the user during the phototherapy may turn off the phototherapeutic system (e.g., the phototherapeutic system 100) though depressing the button 870 by the user when the phototherapeutic system (e.g., the phototherapeutic system 100) is not performing or operating may not necessarily turn on the phototherapeutic system as discussed above with respect to FIG. 1.

In an embodiment, the buttons 815, 825, 835, 845, 855, 865, 870 are manually actuatable elements provided on an exterior surface 805 of the user interface 130. In addition, one or more of the display windows 810, 820, 830, 840, 850, 860 are backlit LCDs and the buttons 815, 825, 835, 845, 855, 865, 870, the display windows 810, 820, 830, 840, 850, 860, or both are recessed from the exterior surface 805 of the user interface 130 to prevent them from being accidentally or inadvertently actuated or damaged. The shape, texture, or both of each button 815, 825, 835, 845, 855, 865, 870 can be unique to that button to enable the user to identify a particular button by its feel. One or more of the buttons 815, 825, 835, 845, 855, 865, 870 or features on the buttons 815, 825, 835, 845, 855, 865, 870 can also be lighted, e.g., backlit, so that they can be seen in a dark room.

Alternatively, in an embodiment, the buttons 815, 825, 835, 845, 855, 865, 870 are virtually elements. In addition, both the buttons 815, 825, 835, 845, 855, 865, 870 and the display windows 810, 820, 830, 840, 850, 860 are presented on an LCD screen provided as the exterior surface 805 of the user interface 130. Further, the LCD screen is a backlit LCD so that one or more of the display windows 810, 820, 830, 840, 850, 860 and the buttons 815, 825, 835, 845, 855, 865, 870 can be lighted and seen in a dark room.

Referring to FIG. 9, yet another exemplary perspective view 900 of the user interface 130 for use in the phototherapeutic system 100 is shown according to yet another embodiment of the disclosure. The user interface 130 includes a display window 910 with or without an indicator of showing the operating time period. The display window 910 is configured to display the operating time period of the phototherapeutic system (e.g., the phototherapeutic system 100). In an embodiment, the initial value of the operating time period is 30 minutes by default. In an embodiment, the initial value of the operating time period may be set to any other suitable length of time. In an embodiment, the initial value of the operating time period will be shown after the one or more parameters (including the operating time period) related to the radiation beams provided by the radiation generator (e.g., the radiation generator 190) are determined based on the user input (e.g., the user input 135), as discussed in greater details below. The value of the operating time period shown in the display window 910 may decrease as time elapses after starting operating the phototherapeutic system (e.g., the phototherapeutic system 100). The value of the operating time period may be adjusted by the user through the button 915. For example, depressing the button 915 clockwise may increase the value of the operating time period as depressing the button 915 counterclockwise may decrease the value of the operating time period shown on the display window 910, or vice versa.

As shown, the user interface 130 includes a plurality of additional indicators (e.g., in form of texts) of parameters related to the user's personal information, for example, the user's personal health conditions. The user's personal information may include, but is not limited to, the user's body temperature, the user's blood pressure, the user's height, and the user's weight. The user interface 130 further includes additional display windows 920, 930, 940, 950, close to each of the additional indicators. The additional display windows 920, 930, 940, 950 are configured to display values, determined and inputted by the user, of the parameters identified by the corresponding neighboring indicators. The default values for the one or more parameters related to the user's personal information are shown in the additional display windows 920, 930, 940, 950, for example, as shown in FIG. 9. The user interface 130 further includes additional buttons 925, 935, 945, 955 near each of the additional display windows 920, 930, 940, 950. The additional buttons 920, 930, 940, 950 are configured to receive the user input (e.g., the user input 135) to adjust the values shown in the neighboring display windows 920, 930, 940, 950. Similar to the button 915, in an embodiment, depressing the buttons 925, 935, 945, 955 clockwise may increase the value shown in the respective neighboring display windows 920, 930, 940, 950, as depressing the buttons 925, 935, 945, 955, 955 counterclockwise may decrease the value shown in the respective neighboring display windows 920, 930, 940, 950, or vice versa. The user's personal information, including the one or more values inputted by the user and shown in the display windows 920, 930, 940, 950 may be transmitted to the radiation control circuit (e.g., the radiation control circuit 160 as shown in FIG. 1), which is further configured to determine the one or more parameters related to the waveforms of the radiation beams provided by the radiation generator (e.g., the radiation generator 190) based on the user input related to the user's personal information. In an embodiment, the value of the operating time period, after determined by the radiation control circuit (e.g., the radiation control circuit) is shown in the display window 910, which may be or may not be further adjusted by the user through the button 915. In an embodiment, the user interface 130 may further include a terminal port 960 to be used to connect to an external computing device or an external memory (not shown) through a connection cable so that the one or more values related to the user's personal information may be communicated to the user interface 130 from the external computing device or the external memory without a need for the user's manual input with respect to the display windows 910, 920, 930, 940, 950 and the buttons 915, 925, 935, 945, 955 in the user interface 130.

The user interface 130 as shown in FIG. 9 further includes a button 970 used to communicate the user's request to turn on or off the phototherapeutic system (e.g., the phototherapeutic system 100). Specifically, depressing the button 970 by the user during the phototherapy may turn off the phototherapeutic system (e.g., the phototherapeutic system 100) though depressing the button 970 by the user when the phototherapeutic system (e.g., the phototherapeutic system 100) is not performing or operating may not necessarily turn on the phototherapeutic system as discussed above with respect to FIG. 1.

In an embodiment, the buttons 915, 925, 935, 945, 955, 970 are manually actuatable elements provided on an exterior surface 905 of the user interface 130. In addition, one or more of the display windows 910, 920, 930, 940, 950 are backlit LCDs and the buttons 915, 925, 935, 945, 955, 970, the display windows 910, 920, 930, 940, 950, or both are recessed from the exterior surface 905 of the user interface 130 to prevent them from being accidentally or inadvertently actuated or damaged. The shape, texture, or both of each button 915, 925, 935, 945, 955, 970 can be unique to that button to enable the user to identify a particular button by its feel. One or more of the buttons 915, 925, 935, 945, 955, 970 or features on the buttons 915, 925, 935, 945, 955, 970 can also be lighted, e.g., backlit, so that they can be seen in a dark room.

Alternatively, in an embodiment, the buttons 915, 925, 935, 945, 955, 970 are virtually elements. In addition, both the buttons 915, 925, 935, 945, 955, 970 and the display windows 910, 920, 930, 940, 950 are presented on an LCD screen provided as the exterior surface 905 of the user interface 130. Further, the LCD screen is a backlit LCD so that one or more of the display windows 910, 920, 930, 940, 950 and the buttons 915, 925, 935, 945, 955, 970 can be lighted and seen in a dark room.

FIGS. 10-13 are example waveforms of radiation beams provided by at least one of the radiation sources in the radiation generator 190 according to an embodiment of the disclosure. In FIGS. 10-13, the horizontal axis represents time, as the vertical axis represents power. The example waveforms shown in FIGS. 10-13 may be provided corresponding to the one or more parameters of the waveforms of the radiation beams provided by the radiation generator, e.g., the radiation generator 190, including the operating time period, the crest power, the average power, the trough power, and the wave frequency, and the wave shape. The one or more parameters of the waveforms may be directly or indirectly obtained from the user input 135 through the user interface 130 as described in FIGS. 7-8. Alternatively or in addition, the one or more parameters of the waveforms may be determined based on the one or more parameters related to the user's personal information as described in FIG. 9.

Figure 10:
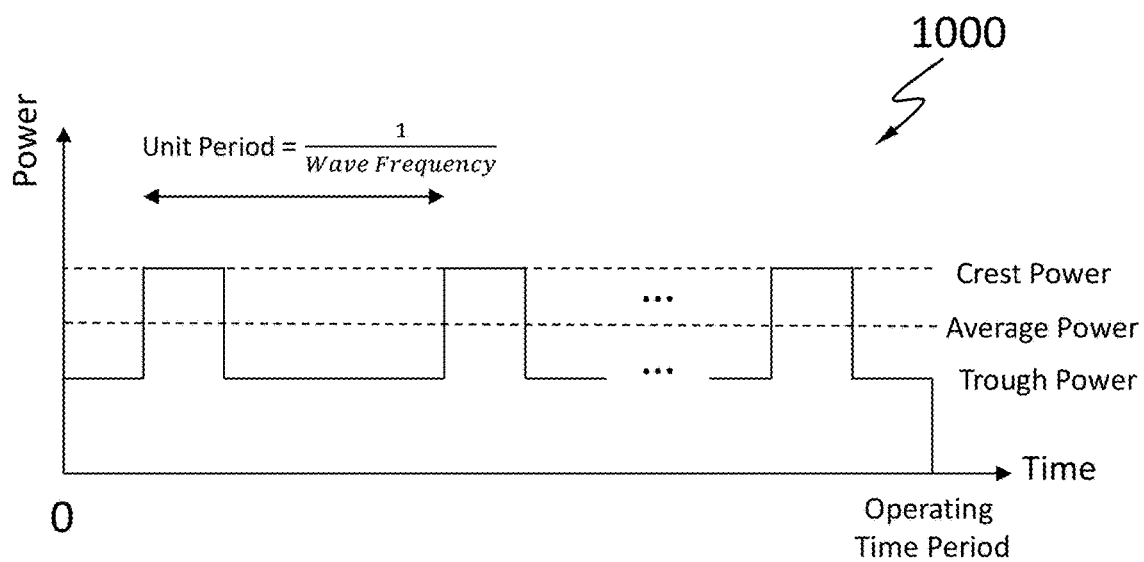
FIG. 10 shows an example waveform of radiation beams provided by a radiation generator according to an embodiment of the disclosure.
Figure 11:
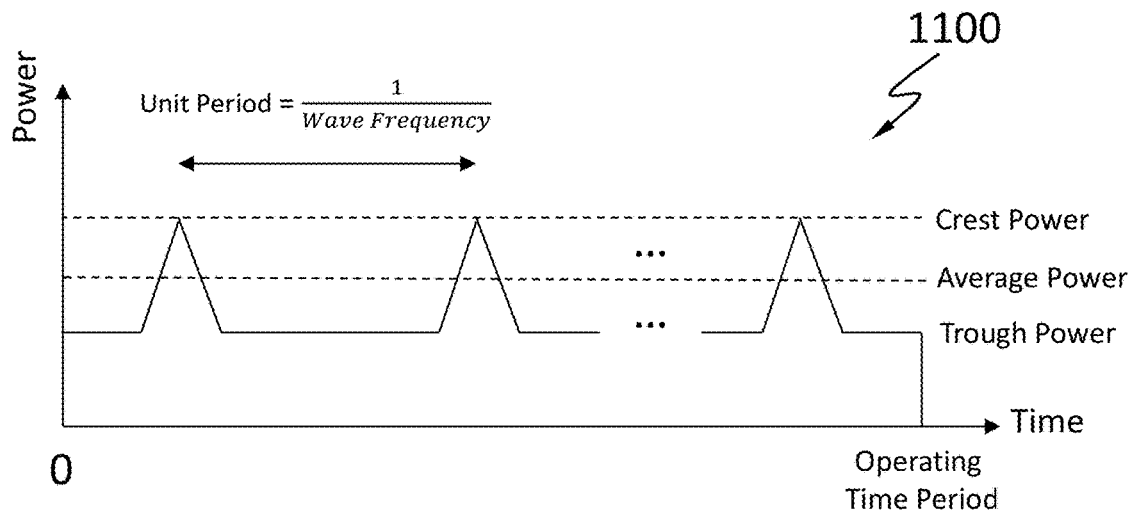
FIG. 11 shows an example waveform of radiation beams provided by a radiation generator according to an embodiment of the disclosure.

In an embodiment, each unit period of the waveforms may include a single wave shape. For example, the single wave shape may be a single rectangle as shown in FIG. 10 or a single triangle as shown in FIG. 11. In some other examples, the single wave shape may be a single sinusoidal shape, a single square, a single semi-circle, or any other suitable shape.

Figure 12:
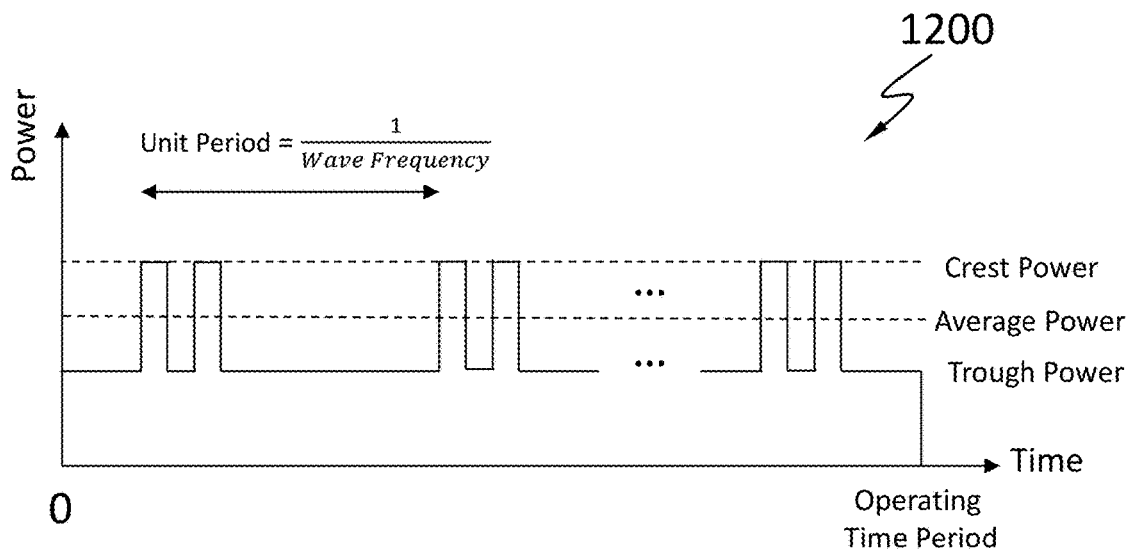
FIG. 12 shows an example waveform of radiation beams provided by a radiation generator according to an embodiment of the disclosure.

In an embodiment, each unit period of the waveforms may include two or more repetitive wave shapes. For example, the two or more repetitive wave shapes may be two or more repetitive rectangles as shown in FIG. 12. In some other examples, the two or more repetitive wave shapes may be two or more repetitive triangles, two or more repetitive sinusoidal shapes, two or more repetitive squares, two or more repetitive semi-circles, or any other suitable shapes.

Figure 13:
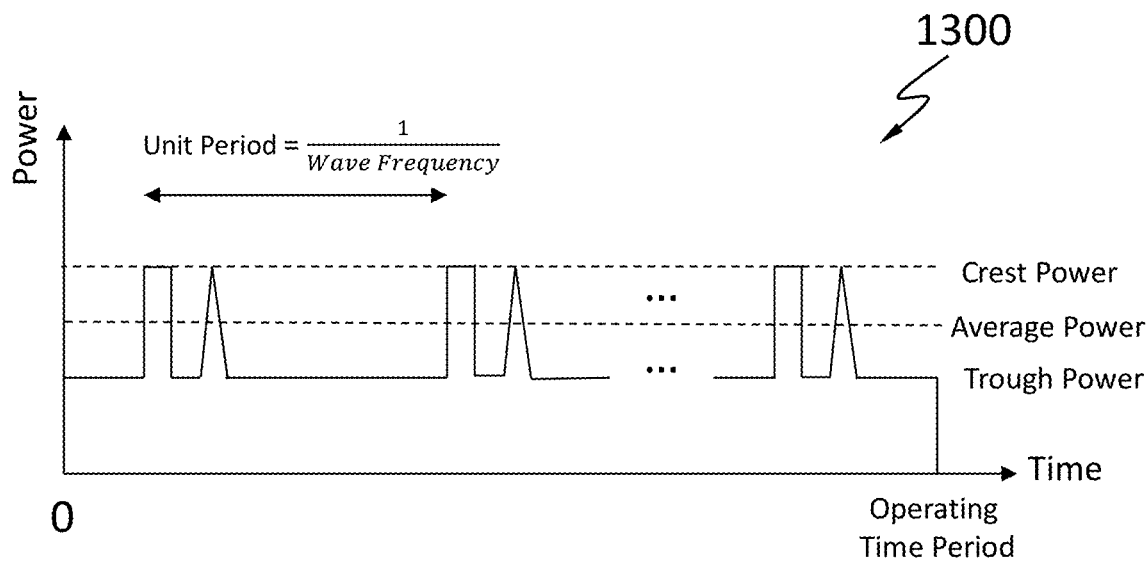
FIG. 13 shows an example waveform of radiation beams provided by a radiation generator according to an embodiment of the disclosure.

In an embodiment, each unit period of the waveforms may include a combination of different wave shapes. For example, the combination of different wave shapes is a combination of a rectangle and a triangle as shown in FIG. 13. In some other examples, the combination of different wave shapes may be any other combination of a rectangle, a triangle, a sinusoidal shape, a square, a semi-circle, and/or any other suitable shapes.

Figure 14:
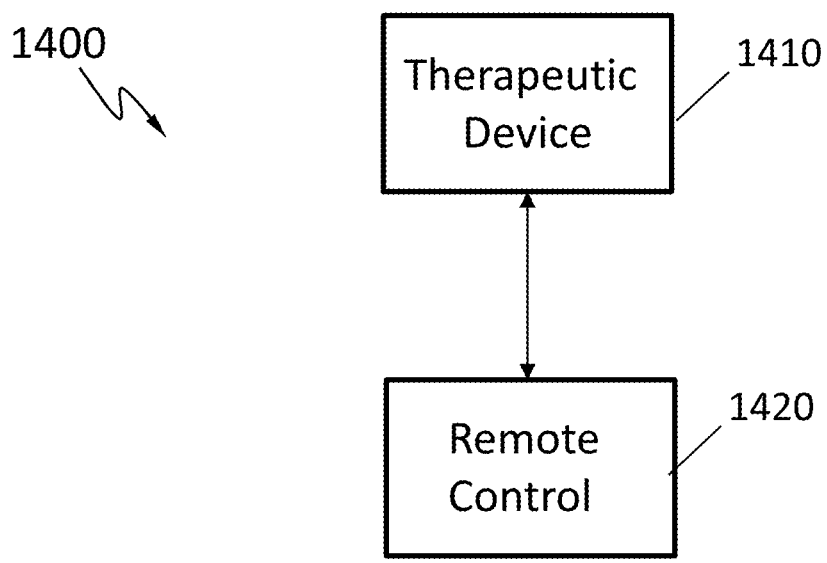
FIG. 14 is a schematic diagram of a phototherapeutic system having a therapeutic device and a remote control according to an embodiment of the disclosure.

In an embodiment, the phototherapeutic system may not be a stand-alone system as shown in FIG. 1. Referring to FIG. 14, a schematic diagram of another phototherapeutic system 1400 having a therapeutic device 1410 and a remote control 1420 is shown according to an embodiment of the disclosure. The therapeutic device 1410 and the remote control 1420 are in communication with each other. In an embodiment, the therapeutic device 1410 and the remote control 1420 are in wireless communication with each other, for example, through WIFI, BLUETOOTH, or any other suitable protocols. In an embodiment, the therapeutic device 1410 and the remote control 1420 are in wired communication with each other, for example, through a connection cable, an optical fiber, a copper wire, or any other suitable means. FIGS. 15-20 shows various examples of the therapeutic devices 1410 and the remote controls 1420 depending on where the switch control circuit (e.g., the switch control circuit 150) and/or the radiation control circuit (e.g., the radiation control circuit 160) are located in the phototherapeutic system 1400.

In an embodiment, the switch control circuit is included in the therapeutic device as the radiation control circuit is included in the remote control. Examples of the therapeutic device and the remote control are illustrated in FIGS. 15-16, respectively.

Figure 15:
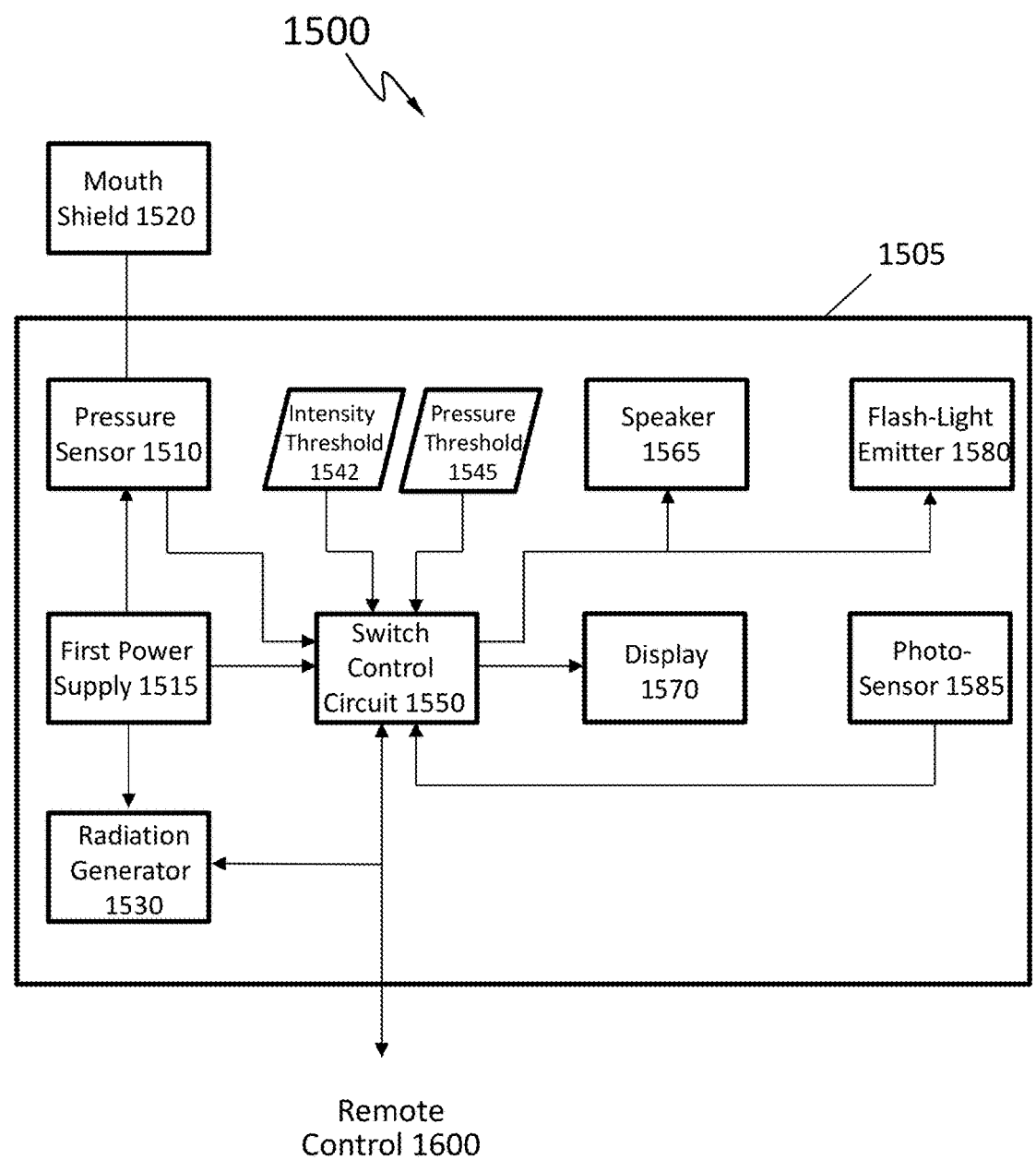
FIG. 15 is a schematic diagram of a therapeutic device according to an embodiment of the disclosure.

Referring to FIG. 15, a schematic diagram of a therapeutic device 1500 is shown according to an embodiment of the disclosure. In an embodiment, the therapeutic device 1500 is the therapeutic device 1410 in FIG. 14. The therapeutic device 1500 is in communication with a remote control 1600 in FIG. 16. As shown, the therapeutic device 1500 includes a housing 1505 and a mouth shield 1520 mounted on the housing 1505. Similar to the housing 105 in FIG. 1, the housing 1505 may be made from any suitable material, such as cleanable ABS/polycarbonate plastic.

The therapeutic device 1500 further includes a plurality of components disposed inside or on an exterior surface of the housing 1505. The plurality of components may be arranged as shown or in any other suitable manner. The plurality of components may include a pressure sensor 1510 coupled to the mouth shield 1520, a first power supply 1515 coupled to the pressure sensor 1510, a radiation generator 1530 coupled to the first power supply 1515 and in communication with the remote control 1600, a switch control circuit 1550 in communication with the remote control 1600 and coupled to the pressure sensor 1510, and the first power supply 1515, a speaker 1565 coupled to the switch control circuit 1550, a display 1570 coupled to the switch control circuit 1550, a flash-light emitter 1580 coupled to the switch control circuit 1550, and a photo-sensor 1585 coupled to the switch control circuit 1550. The therapeutic device 1500 further includes a memory (not shown) configured to store a plurality of thresholds including an intensity threshold 1542 and a pressure threshold 1545, which are accessible by the switch control circuit 1550. The mouth shield 1520, the pressure sensor 1510, the first power supply 1515, the radiation generator 1530, the intensity threshold 1542, the pressure threshold 1545, the switch control circuit 1550, the speaker 1565, the display 1570, the flash-light emitter 1580, and the photo-sensor 1585 may be substantially similar to the mouth shield 120, the pressure sensor 110, the power supply 115, the radiation generator 190, the intensity threshold 140, the pressure threshold 145, the switch control circuit 150, the speaker 165, the display 170, the flash-light emitter 180, and the photo-sensor 185.

Figure 16:
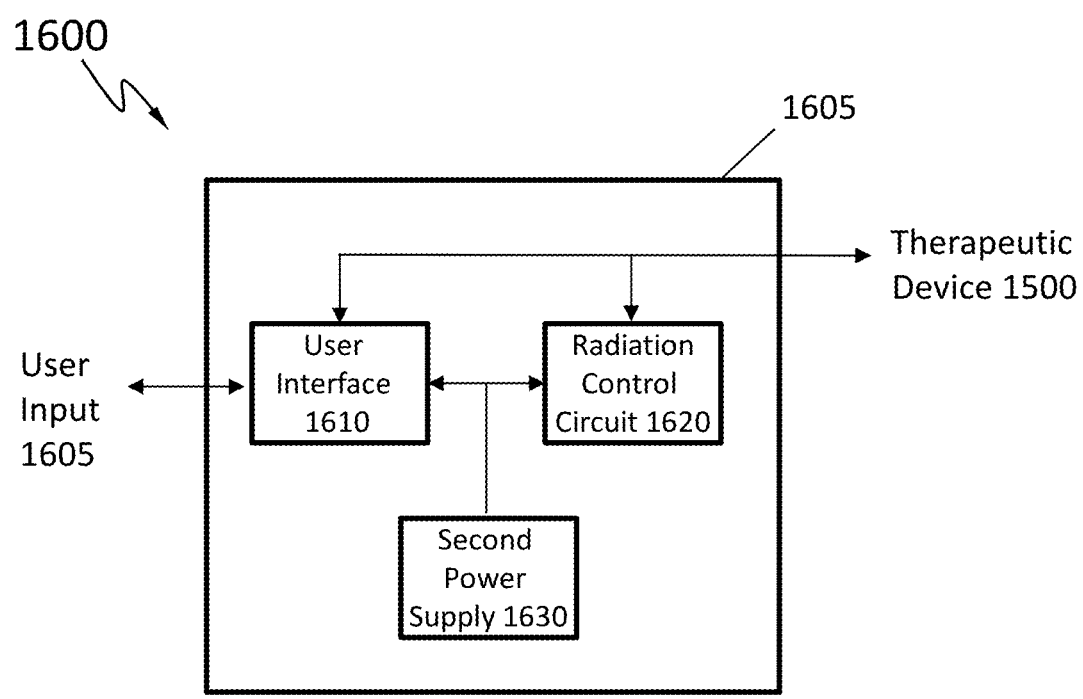
FIG. 16 is a schematic diagram of a remote control according to an embodiment of the disclosure.

Referring to FIG. 16, a schematic diagram of the remote control 1600 is shown according to an embodiment of the disclosure. In an embodiment, the remote control 1600 is the remote control 1420 in FIG. 14. As shown, the remote control 1600 may include a housing 1605. The housing 1605 of the remote control 1600 may be made from any suitable material, such as cleanable ABS/polycarbonate plastic. The remote control 1600 may further include a plurality of components disposed inside or on an exterior surface of the remote control 1600. The plurality of components includes a user interface 1610 configured to receive a user input 1605, a radiation control circuit 1620 coupled to the user interface 1610, and a second power supply 1630 coupled to the user interface 1610 and the radiation control circuit 1620. The user interface 1610 and the radiation control circuit 1620 are both in communication with the therapeutic device 1500. The user interface 1610, the radiation control circuit 1620, the second power supply 1630, and the user input 1605 may be substantially similar to, the user interface 130, the radiation control circuit 160, the power supply 115, and the user input 135.

In an embodiment, both the switch control circuit and the radiation control circuit are included in the remote control. Examples of the therapeutic device and the remote control are illustrated in FIGS. 17-18, respectively.

Figure 17:
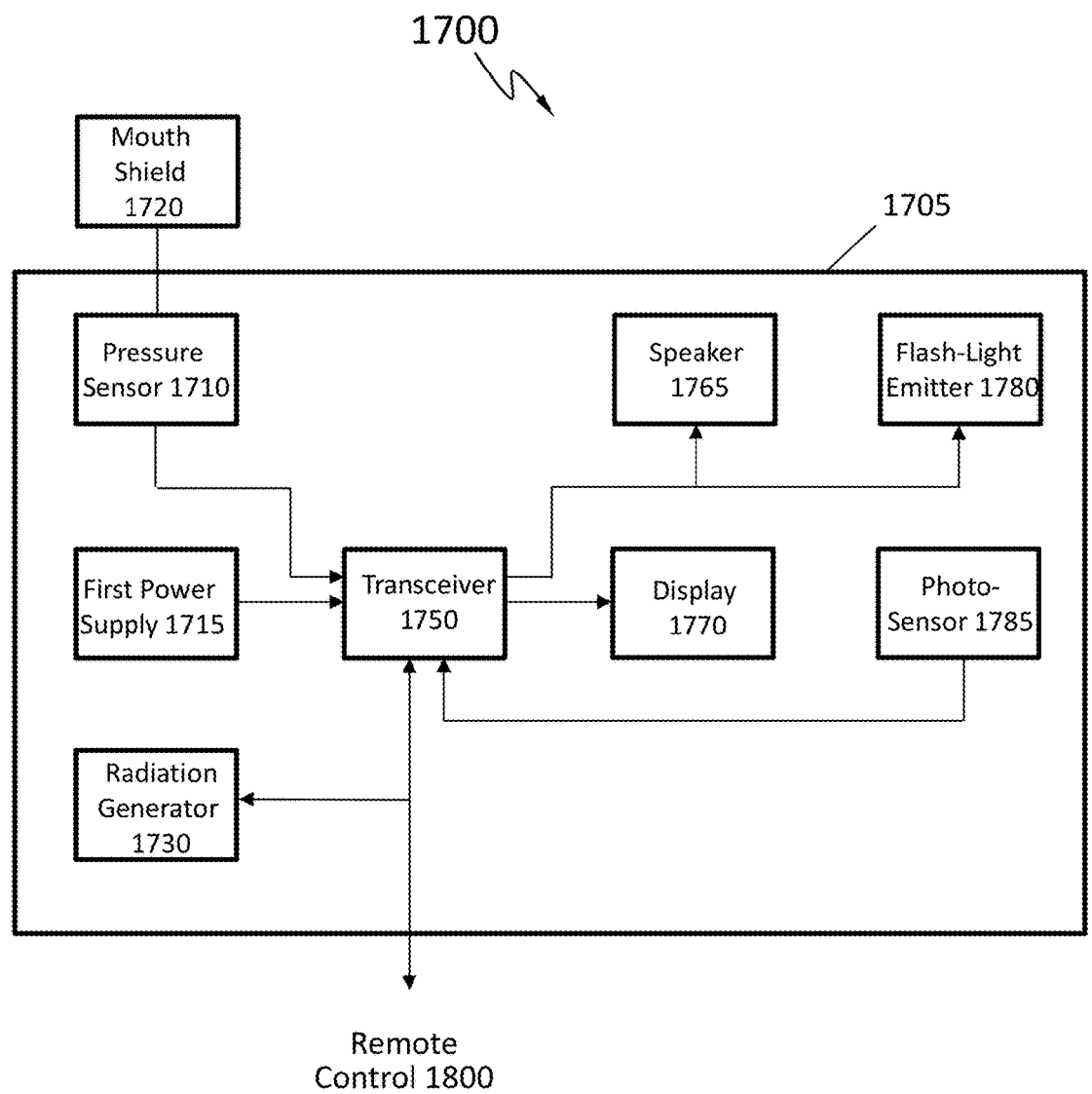
FIG. 17 is a schematic diagram of a therapeutic device according to an embodiment of the disclosure.
Figure 18:
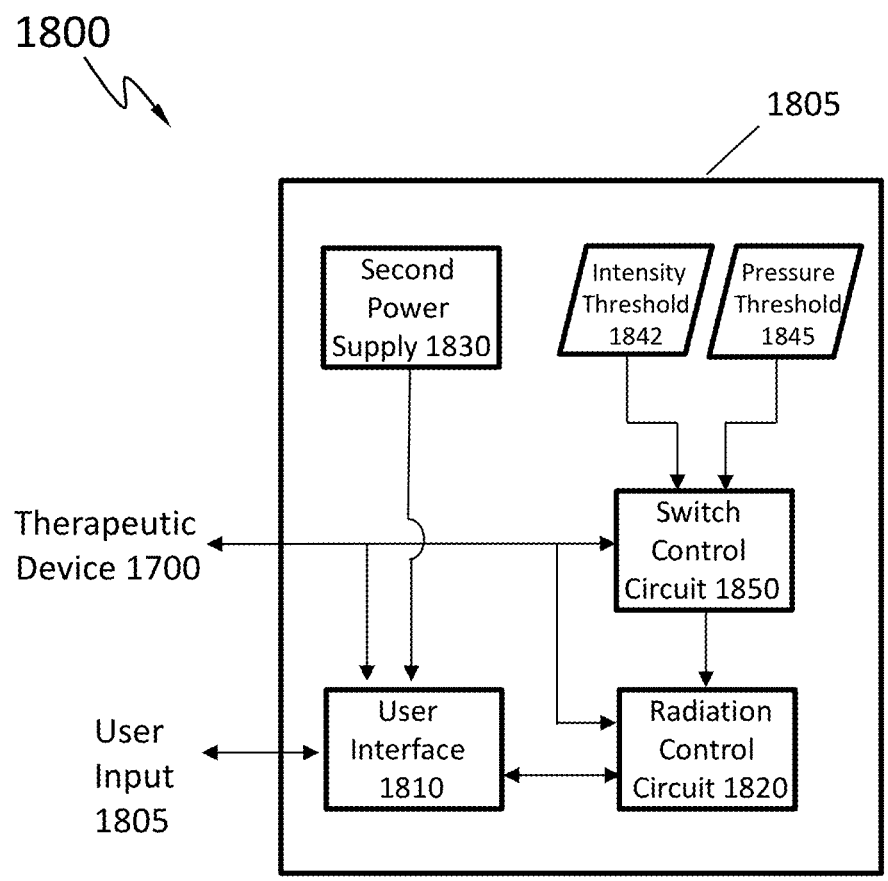
FIG. 18 is a schematic diagram of a remote control according to an embodiment of the disclosure.

Referring to FIG. 17, a schematic diagram of a therapeutic device 1700 is shown according to an embodiment of the disclosure. In an embodiment, the therapeutic device 1700 is the therapeutic device 1410 in FIG. 14. The therapeutic device 1700 is in communication with a remote control 1800 in FIG. 18. As shown, the therapeutic device 1700 includes a housing 1705 and a mouth shield 1720 mounted on the housing 1705. Similar to the housing 105 in FIG. 1, the housing 1705 may be made from any suitable material, such as cleanable ABS/polycarbonate plastic.

The therapeutic device 1700 further includes a plurality of components disposed inside or on an exterior surface of the housing 1705. The plurality of components may be arranged as shown or in any other suitable manner. The plurality of components may include a transceiver 1750 coupled to each of the plurality of other components in the therapeutic device 1700. The transceiver 1750 may be configured to transmit signals or information from one or more of the plurality of components in the therapeutic device 1700 to the remote control 1800. For example, the transceiver 1750 may be configured to transmit one or more values provided by the one or more sensors to the remote control 1800. The one or more sensors may include, but are not limited to, a photo-sensor 1785, a pressure sensor 1710, a distance sensor (not shown), a temperature sensor (not shown), or any combination thereof. In addition, the transceiver 1750 may be configured to transmit signals or information from the remote control 1800 to one or more of the plurality of components, for example, a radiation generator 1730 and one or more output components in the therapeutic device 1700. The one or more output components may include, but are not limited to, a speaker 1765, a flash-light emitter 1780, and a display 1770.

As shown, the plurality of components may further include the pressure sensor 1710 coupled to the mouth shield 1720 and the transceiver 1750, a first power supply 1715 coupled to the transceiver 1750, the radiation generator 1730 coupled to the transceiver 1750 and in communication with the remote control 1800, the speaker 1765 coupled to the transceiver 1750, the display 1770 coupled to the transceiver 1750, the flash-light emitter 1780 coupled to the transceiver 1750, and the photo-sensor 1785 coupled to the transceiver 1750. The mouth shield 1720, the pressure sensor 1710, the first power supply 1715, the radiation generator 1730, the speaker 1765, the display 1770, the flash-light emitter 1780, and the photo-sensor 1785 may be substantially similar to the mouth shield 120, the pressure sensor 110, the power supply 115, the radiation generator 190, the speaker 165, the display 170, the flash-light emitter 180, and the photo-sensor 185.

Referring to FIG. 18, a schematic diagram of the remote control 1800 is shown according to an embodiment of the disclosure. In an embodiment, the remote control 1800 is the remote control 1420 in FIG. 14. As shown, the remote control 1800 may include a housing 1805. The housing 1805 of the remote control 1800 may be made from any suitable material, such as cleanable ABS/polycarbonate plastic. The remote control 1800 may further include a plurality of components disposed inside or on an exterior surface of the remote control 1800. The plurality of components includes a user interface 1810 configured to receive a user input 1805, a radiation control circuit 1820 coupled to the user interface 1810, a switch control circuit 1850 coupled to the user interface 1810 and the radiation control circuit 1820, and a second power supply 1830 coupled to the user interface 1810. The user interface 1810, the radiation control circuit 1820, and the switch control circuit 1850 are all in communication with the therapeutic device 1700. The remote control 1800 further includes a memory (not shown) configured to store a plurality of thresholds including an intensity threshold 1842 and a pressure threshold 1845, which are accessible by the switch control circuit 1850. The user interface 1810, the radiation control circuit 1820, the switch control circuit 1850, the second power supply 1830, the intensity threshold 1842, the pressure threshold 1845, and the user input 1805 may be substantially similar to the user interface 130, the radiation control circuit 160, the switch control circuit 150, the power supply 115, the intensity threshold 140, the pressure threshold 145, and the user input 135 in FIG. 1. In an embodiment, the switch control circuit 1850 and the radiation control circuit 1820 are separate components in the remote control 1800 as shown in FIG. 18. In an embodiment, the switch control circuit 1850 and the radiation control circuit 1820 may be combined into, or implemented on, a single control circuit.

In an embodiment, the switch control circuit is included in the remote control as the radiation control circuit is included in the therapeutic device. Examples of the therapeutic device and the remote control are illustrated in FIGS. 19-20, respectively.

Figure 19:
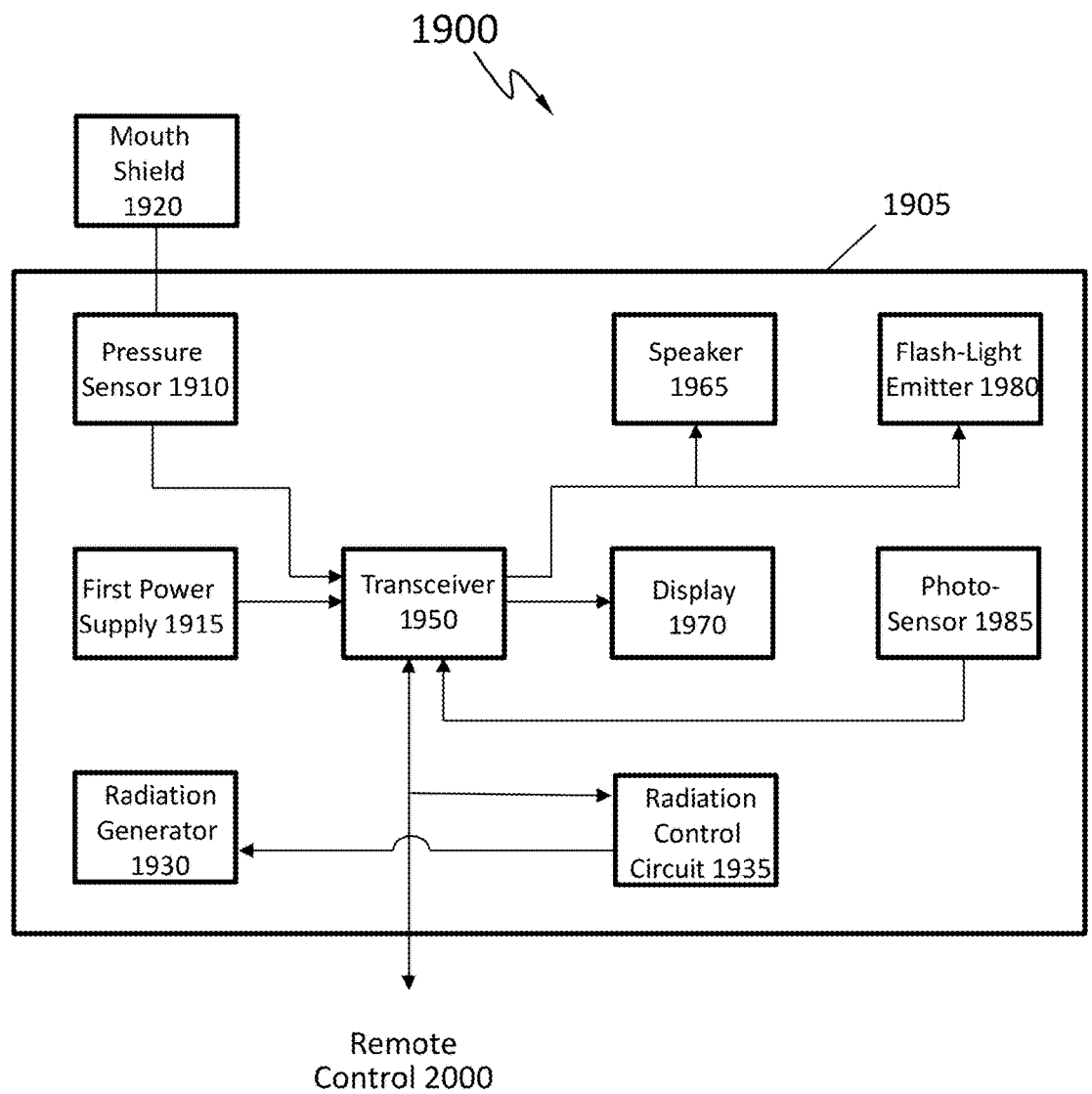
FIG. 19 is a schematic diagram of a therapeutic device according to an embodiment of the disclosure.
Figure 20:
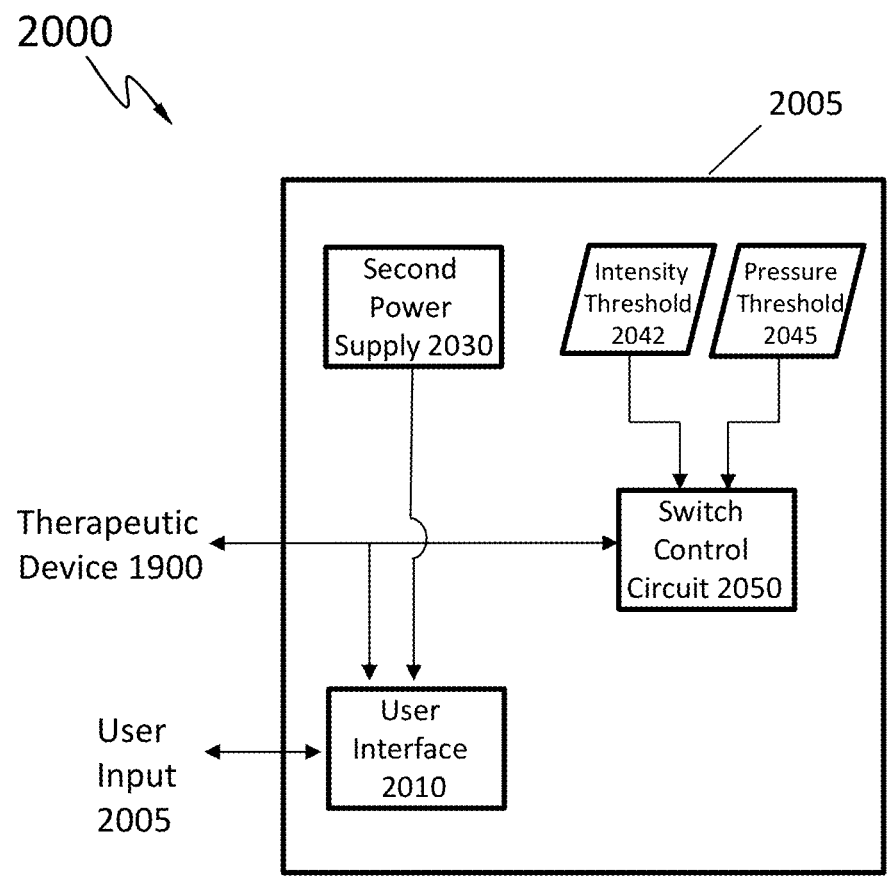
FIG. 20 is a schematic diagram of a remote control according to an embodiment of the disclosure.

Referring to FIG. 19, a schematic diagram of a therapeutic device 1900 is shown according to an embodiment of the disclosure. In an embodiment, the therapeutic device 1900 is the therapeutic device 1410 in FIG. 14. The therapeutic device 1900 is in communication with a remote control 2000 in FIG. 20. As shown, the therapeutic device 1900 includes a housing 1905 and a mouth shield 1920 mounted on the housing 1905. Similar to the housing 105 in FIG. 1, the housing 1905 may be made from any suitable material, such as cleanable ABS/polycarbonate plastic.

The therapeutic device 1900 further includes a plurality of components disposed inside or on an exterior surface of the housing 1905. The plurality of components may be arranged as shown or in any other suitable manner. The plurality of components may include a transceiver 1950 coupled to each of the plurality of other components in the therapeutic device 1900. The transceiver 1950 may be substantially similar to the transceiver 1750 in FIG. 17. The transceiver 1950 may be configured to transmit signals or information from one or more of the plurality of components in the therapeutic device 1900 to the remote control 2000. For example, the transceiver 1950 may be configured to transmit one or more values provided by the one or more sensors to the remote control 2000. The one or more sensors may include, but are not limited to, a photo-sensor 1985, a pressure sensor 1910, a distance sensor (not shown), a temperature sensor (not shown), or any combination thereof. In addition, the transceiver 1950 may be configured to transmit signals or information from the remote control 2000 to one or more of the plurality of components, for example, a radiation control circuit 1935 and one or more output components in the therapeutic device 1900. The one or more output components may include, but are not limited to, a speaker 1965, a flash-light emitter 1980, and a display 1970.

The plurality of components may further include the pressure sensor 1910 coupled to the mouth shield 1920 and the transceiver 1950, a first power supply 1915 coupled to the transceiver 1950, a radiation generator 1930 coupled to the transceiver 1950 and in communication with the remote control 2000, the speaker 1965 coupled to the transceiver 1950, the display 1970 coupled to the transceiver 1950, the flash-light emitter 1980 coupled to the transceiver 1950, the photo-sensor 1985 coupled to the transceiver 1950, and the radiation control circuit 1935 coupled to the radiation generator 1930. The radiation control circuit 1935 and the transceiver 1950 are both in communication with the remote control 2000. The mouth shield 1920, the pressure sensor 1910, the first power supply 1915, the radiation generator 1930, the speaker 1965, the display 1970, the flash-light emitter 1980, the photo-sensor 1985, and the radiation control circuit 1935 may be substantially similar to the mouth shield 120, the pressure sensor 110, the power supply 115, the radiation generator 190, the speaker 165, the display 170, the flash-light emitter 180, the photo-sensor 185, and the radiation control circuit 160 in FIG. 1.

Referring to FIG. 20, a schematic diagram of the remote control 2000 is shown according to an embodiment of the disclosure. In an embodiment, the remote control 2000 is the remote control 1420 in FIG. 14. As shown, the remote control 2000 may include a housing 2005. The housing 2005 of the remote control 2000 may be made from any suitable material, such as cleanable ABS/polycarbonate plastic. The remote control 2000 may further include a plurality of components disposed inside or on an exterior surface of the remote control 2000. The plurality of components includes a user interface 2010 configured to receive a user input 2005, a switch control circuit 2050 coupled to the user interface 2010, and a second power supply 2030 coupled to the user interface 2010. The user interface 2010, the switch control circuit 2050 are both in communication with the therapeutic device 1900. The remote control 2000 further includes a memory (not shown) configured to store a plurality of thresholds including an intensity threshold 2042 and a pressure threshold 2045, which are accessible by the switch control circuit 2050. The user interface 2010, the switch control circuit 2050, the second power supply 2030, the intensity threshold 2042, the pressure threshold 2045, and the user input 2005 may be substantially similar to the user interface 130, the switch control circuit 150, the power supply 115, the intensity threshold 140, the pressure threshold 145, and the user input 135 in FIG. 1.

Figure 21:
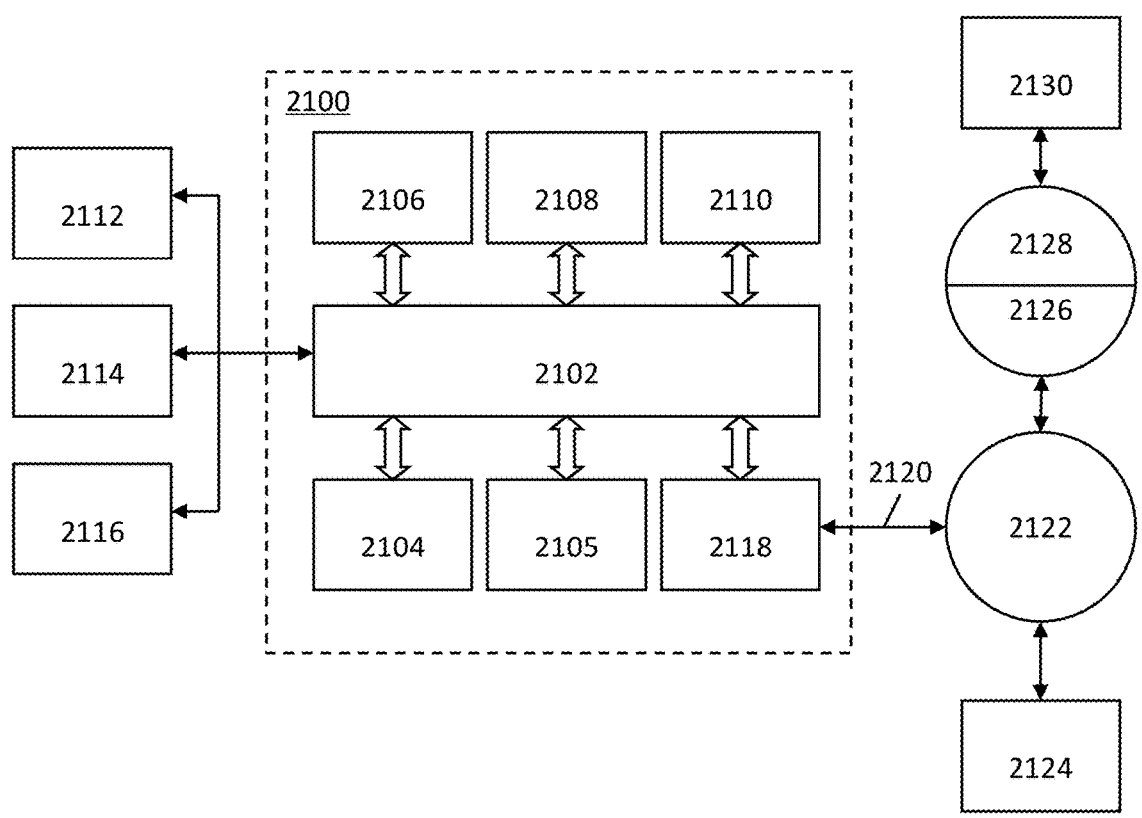
FIG. 21 is a general computer architecture on which the present disclosure can be implemented.

Referring to FIG. 21, a computer system 2100 is shown. The computer system 2100 may be similar to the switch control circuits 150, 1550, 1850, 2050 and/or the radiation control circuit 160, 1620, 1820, 1935. The computer system 2100 includes a bus 2102 or other communication mechanism to communicate information, and a processor 2104 (or multiple processors 2104 and 2105) coupled with the bus 2102 to process information. In an embodiment, the computer system 2100 includes a main memory 2106, such as a random-access memory (RAM) or other dynamic storage device, coupled to the bus 2102 to store information and instructions to be executed by the processor 2104. The main memory 2106 may be used to store temporary variables or other intermediate information during execution of instructions to be executed by the processor 2104. In an embodiment, the computer system 2100 includes a read only memory (ROM) 2108 or other static storage device coupled to the bus 2102 to store essentially static information and instructions for the processor 2104. In an embodiment, a storage device 2110, such as a solid-state drive, magnetic disk or optical disk, is provided and coupled to the bus 2102 to store information and instructions.

The computer system 2100 may be coupled via the bus 2102 to a display 2112, such as a cathode ray tube (CRT) or flat panel or touch panel display, to display information to a computer user. In an embodiment, an input device 2114, including or providing alphanumeric and other keys, is coupled to the bus 2102 to communicate information and command selections to the processor 2104. Another type of user input device is a cursor controller 2116, such as a mouse, a trackball, or cursor direction keys, to communicate direction information and command selections to the processor 2104 and to control cursor movement on the display 2112. A touch panel (screen) display may also be used as an input device.

The computer system 2100 may be suitable to implement methods as described herein in response to the processor 2104 executing one or more sequences of one or more instructions contained in, e.g., the main memory 2106. Such instructions may be read into the main memory 2106 from another computer-readable medium, such as the storage device 2110. In an embodiment, execution of sequences of instructions contained in the main memory 2106 causes the processor 2104 to perform process steps described herein. One or more processors in a multi-processing arrangement may be employed to execute the sequences of instructions contained in the main memory 2106. In an embodiment, a hard-wired circuitry may be used in place of or in combination with software instructions. Thus, embodiments are not limited to any specific combination of hardware circuitry and software.

The term "computer-readable medium" as used herein refers to any medium that participates in providing instructions to the processor 2104 for execution. Such a medium may take many forms, including but not limited to, non-volatile media, volatile media, and transmission media. Non-volatile media include, for example, solid state, optical or magnetic disks, such as the storage device 2110. Volatile media include dynamic memory, such as the main memory 2106. Non-volatile and volatile media are considered non-transitory. Non-transitory transmission media include coaxial cables, copper wire and fiber optics, including the wires that comprise the bus 2102. Transmission media can also take the form of acoustic or light waves, such as those generated during RF and infrared data communications. Common forms of computer-readable media include, for example, a floppy disk, hard disk, magnetic tape, any other magnetic medium, a CD-ROM, DVD, any other optical medium, punch cards, paper tapes, any other physical medium with patterns of holes, an RAM, a PROM, an EPROM, a FLASH-EPROM, a solid-state disk or any other memory chip or cartridge, a carrier wave as described herein, or any other medium from which a computer can read.

Various forms of computer readable media may be involved in carrying one or more sequences of one or more instructions to the processor 2104 for execution. For example, the instructions may initially be borne on a magnetic disk of a remote computer. The remote computer can load the instructions into its dynamic memory and send the instructions over communications medium (e.g., by line or wireless). The computer system 2100 can receive the transmitted data and place the data on the bus 2102. The bus 2102 carries the data to the main memory 2106, from which the processor 2104 retrieves and executes the instructions. The instructions received by the main memory 2106 may optionally be stored on the storage device 2110 either before or after execution by the processor 2104.

The computer system 2100 may also include a communication interface 2118 coupled to the bus 2102. The communication interface 2118 provides a two-way data communication coupling to a network link 2120 that is connected to a local network 2122. For example, the communication interface 2118 may be an integrated service digital network (ISDN) card or a modem to provide a data communication connection to a corresponding type of line. As another example, the communication interface 2118 may be a local area network (LAN) card to provide a data communication connection to a compatible LAN. Wireless links may also be implemented. In any such implementation, the communication interface 2118 sends and receives electrical, electromagnetic or optical signals that carry digital data streams representing various types of information.

The network link 2120 typically provides data communication through one or more networks to other data devices. For example, the network link 2120 may provide a connection through the local network 2122 to a host computer 2124 or to data equipment operated by an Internet Service Provider (ISP) 2126. The ISP 2126 in turn provides data communication services through the worldwide packet data communication network, commonly referred to as the internet 2128. The local network 2122 and the internet 2128 both use electrical, electromagnetic or optical signals that carry digital data streams. The signals through the various networks and the signals on the network link 2120 and through the communication interface 2118, which carry the digital data to and from the computer system 2100, are example forms of carrier waves transporting the information.

The computer system 2100 can send messages and receive data, including program code, through the network(s), the network link 2120, and the communication interface 2118. In the internet example, a server 2130 might transmit a requested code for an application program through the internet 2128, the ISP 2126, the local network 2122 and the communication interface 2118. In accordance with one or more embodiments, one such downloaded application implements a method as described herein. The received code may be executed by the processor 2104 as it is received, and/or stored in the storage device 2110, or other non-volatile storage for later execution. In this manner, the computer system 2100 may obtain application code.

An embodiment may take the form of a computer program containing one or more sequences of machine-readable instructions describing a method as disclosed herein, or a data storage medium (e.g. semiconductor memory, magnetic or optical disk) having such a computer program stored therein. Further, the machine-readable instructions may be embodied in two or more computer programs. The two or more computer programs may be stored on one or more different memories and/or data storage media.

Any controllers described herein may each or in combination be operable when the one or more computer programs are read by one or more computer processors located within at least one component of the phototherapeutic system, the therapeutic device, and/or the remote control. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So, the controller(s) may operate according the machine-readable instructions of one or more computer programs.

Figure 22:
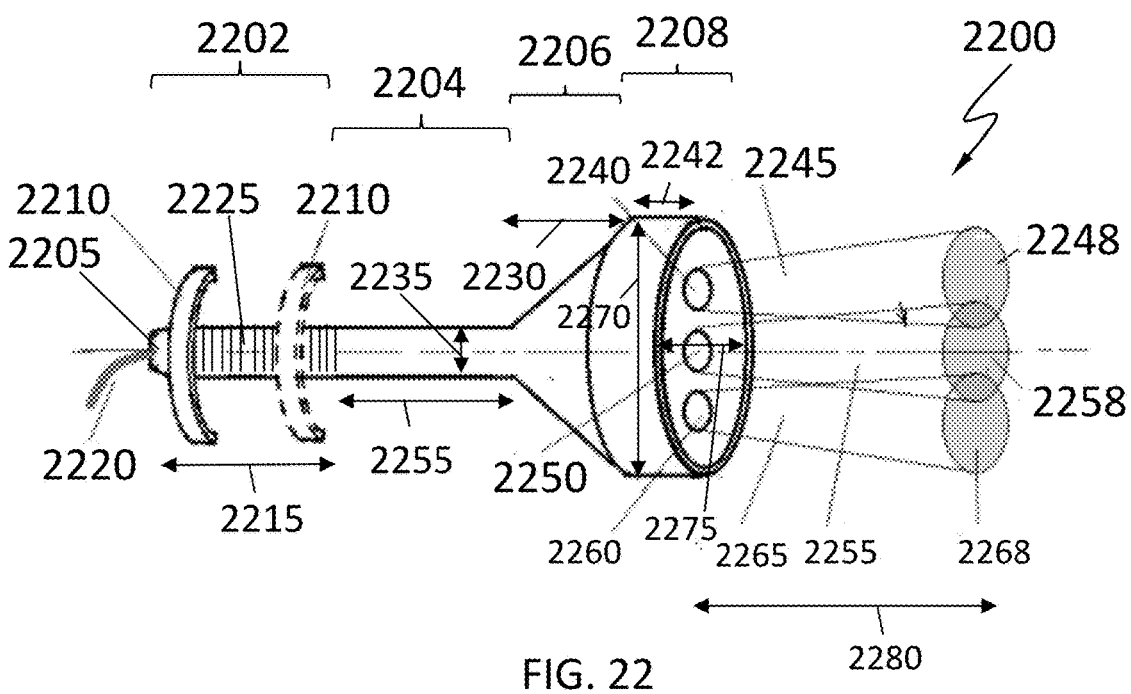
FIG. 22 schematically depicts an embodiment of a phototherapeutic device.

Referring to FIG. 22, an embodiment of a therapeutic device 2200 is schematically depicted. The therapeutic device 2200 may be substantially similar to the therapeutic devices 1410, 1500, 1700, 1900. As shown, the therapeutic device 2200 may be divided into four portions: a first portion 2202, a second portion 2204 coupled to the first portion 2202, a third portion 2206 coupled to the second portion 2204, and a fourth portion 2208 coupled to the third portion 2206.

The first portion 2202 of the therapeutic device 2200 may receive a pressure directly or indirectly from the user's mouth during the phototherapy. The pressure keeps the fourth portion 2208 of the therapeutic device 2200 inside the user's mouth and prevents the fourth portion 2208 of the therapeutic system 2200 from moving during the phototherapy. In an embodiment, the first portion 2202 of the therapeutic device 2200 includes a track 2225 attached on the therapeutic device 2200. As shown, the track 2225 has a saw-tooth shape. In some examples, the user's mouth may apply the pressure on the first portion 2202 of the therapeutic device 2200 by biting between adjacent teeth of the track 2225. In some examples, the mouth shield 2210 may be mounted on the first portion 2202 of the therapeutic device 2200 through the track 2225. In addition, the mouth shield 2210 may slide along through the track 2225. For example, the mouth shield 2210 may slide from one position (denoted by solid lines) to another position (denoted by dotted lines) along the track 2225 as shown in FIG. 22. As such, the user's mouth may apply the pressure on the first portion 2202 of the therapeutic device 2200 by biting the mouth shield 2210, which may assist keeping the user's mouth wide open while holding the position of the phototherapeutic device 2200 during the phototherapy, thus preventing the phototherapeutic device 2200 from slipping into, or being swallowed by the user into the user's digestive canal. Alternatively as described with respect to FIG. 1, the track 2225 may have any other suitable configurations. For example, the track 2225 may include a plurality of columns arranged in a two-dimensional array or any other suitable patterns. In this example, the user's mouth may apply the pressure on the first portion 2202 of the therapeutic device 2200 by biting between adjacent columns of the track 2225. In an embodiment, the first portion 2202 of the therapeutic device 2200 has a length 2215 between 2 cm and 4 cm, a thickness 2235 between 0.8 cm and 1 cm, and a width (not shown) between 1.5 cm and 2 cm. In an embodiment, a terminal 2205 may be provided and coupled to a cable 2220 at an end of the first portion 2202 of the therapeutic device 2200 as shown in FIG. 22. In an embodiment, the cable 2220 may be a portion of a battery recharger. Accordingly, the terminal 2205 may be used for connecting the battery recharger to the batteries (e.g., the first power supply 1515, 1715, 1915 included in the therapeutic device 1500, 1700, 1900) in the therapeutic device 2200. Alternatively or in addition, the cable 2220 may be a connection cable. Accordingly, the terminal 2205 may be used for connecting the therapeutic device 2200 with a respective remote control (not shown) through the cable 2220.

The second portion 2204 of the therapeutic device 2200 may have a length 2255 between 2 cm and 3 cm, the thickness 2235 between 0.8 cm and 1 cm, and a width (not shown) between 1.5 cm and 2 cm. In an embodiment, the second portion 2204 may have a rectangular cross-section. The third portion 2206 of the therapeutic device 2200 may have a length 2230 between 0.8 cm and 1 cm. The cross-section of the third portion 2206 may have a shape transitioned from a rectangle to an ellipse.

The fourth portion 2208 of the therapeutic device 2200 has a length 2242 between 0.8 cm and 2.5 cm. The cross-section of the fourth portion 2208 is an ellipse having a major axis 2270 with a length between 3 cm and 4 cm, and a minor axis 2275 with a length between 1 cm and 2 cm. The fourth portion 2208 of the therapeutic device 2200 includes a radiation generator. As shown, the radiation generator includes three radiation sources, e.g., a first radiation source 2240, a second radiation source 2250, and a third radiation source 2260. The first radiation source 2240 provides a first radiation beam 2245 corresponding to a first projection 2248 of illumination at a distance 2280 between 3 cm and 3.5 cm from the first radiation source 2240. The second radiation source 2250 provides a second radiation beam 2255 corresponding to a second projection 2258 of illumination at the distance 2280 from the second radiation source 2250. The third radiation source 2260 provides a third radiation beam 2265 corresponding to a third projection 2268 of illuminations at the distance 2280 from the third radiation source 2260. In an embodiment, the first radiation beam 2245, the second radiation beam 2255, and the third radiation beam 2265 may be provided at the same time. In an embodiment, the first radiation beam 2245, the second radiation beam 2255, and the third radiation beam 2265 may be provided at different times. As shown, the first projection 2248 of illuminations is partially overlapped with the second projection 2258 of illuminations, as the second projection 2258 of illuminations is partially overlapped with the third projection 2268 of illumination. It should be noted that FIG. 22 is only for illustrating purpose, and the number of the radiation sources included in the radiation generator of the therapeutic device 2200 may not be limiting. Further, as shown in FIG. 22, the three radiation sources 2240, 2250, 2260 are arranged in a column. However, in some other examples, the radiation sources in the radiation generator may be arranged in a row, in a two-dimensional array, in a three-dimensional array, or in any other suitable manners.

Figure 23:
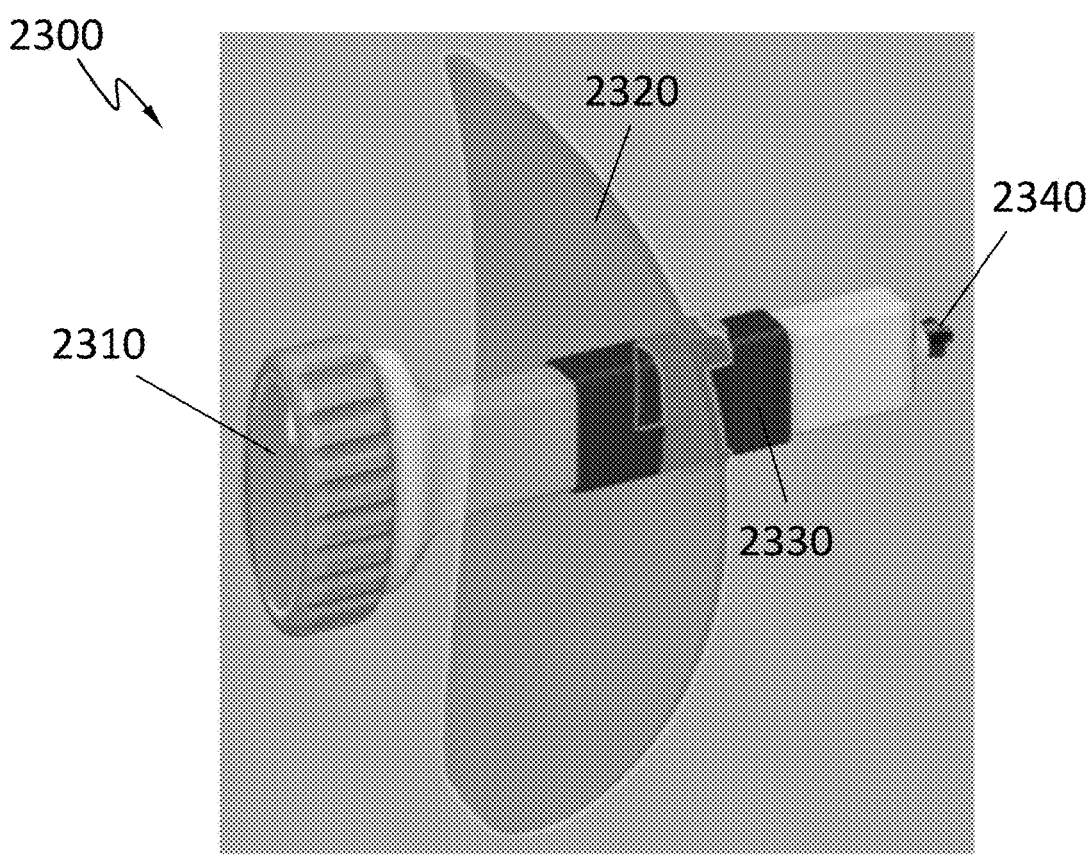
FIG. 23 schematically depicts an embodiment of a phototherapeutic device.

Referring to FIG. 23, an embodiment of another therapeutic device 2300 is schematically depicted. As shown, the therapeutic device 2300 includes a radiation generator 2310, a track 2330 attached on an exterior surface of the therapeutic device 2300, and a mouth shield 2320 mounted on the track 2330. In an embodiment, the track 2330 has a saw-tooth shape. In an embodiment, the mouth shield 2320 can slide along a portion of the therapeutic device 2300 through the track 2330. In an embodiment, the track 2330 may have any other suitable configurations. For example, the track 2330 may include a plurality of columns arranged in a two-dimensional array or any other suitable patterns. Further as shown in FIG. 23, the mouth shield 2320 has a fin shape. In addition, the therapeutic device 2300 includes a terminal 2340 at an end of the therapeutic device 2300. In an embodiment, the terminal 2340 may be used for connecting a battery recharger to batteries (e.g., the first power supply 1515, 1715, 1915 included in the therapeutic device 1500, 1700, 1900) in the therapeutic device 2300. Alternatively or in addition, the terminal 2340 may be used for connecting the therapeutic device 2230 with a respective remote control (not shown) through a connection cable (not shown).

Figure 24:
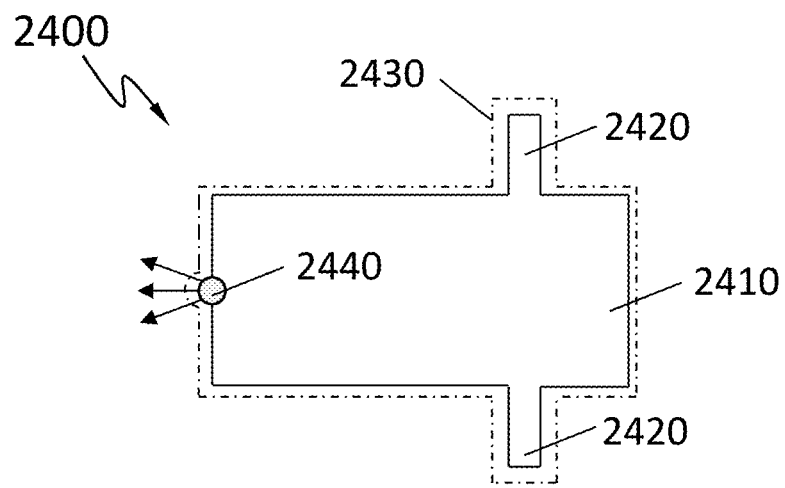
FIG. 24 is a schematic diagram of a phototherapeutic system according to an embodiment of the disclosure.

Referring to FIG. 24, a schematic diagram of a phototherapeutic system 2400 is shown according to an embodiment of the disclosure. As shown, the phototherapeutic system 2400 includes a therapeutic device 2410. The therapeutic device 2410 may be substantially similar to the therapeutic devices 1410, 1500, 1700, 1900. As shown, the therapeutic device 2410 includes a radiation generator 2440. The therapeutic device 2410 further includes a mouth shield 2420 mounted on an exterior surface of the therapeutic device 2410. In addition, the phototherapeutic system 2400 further includes a protection sleeve 2430 configured to cover the therapeutic device 2410 including the mouth shield 2420 and the radiation generator 2440. Further, the protection sleeve 2430 may be made from any suitable materials that allows the plurality of radiation beams provided by the radiation generator 2440 to pass through the protection sleeve 2430. This is done so as to prevent the user of the phototherapeutic system 2400 from contaminating the mouth shield 2420, the radiation generator 2440, and/or any other part of the phototherapeutic system 2400 while ensuring the normal operating of the phototherapeutic system when in use.

Figure 25:
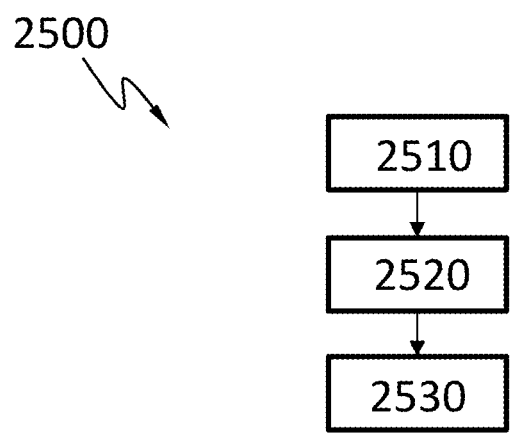
FIG. 25 is a flowchart of an exemplary process for performing phototherapy using a phototherapeutic system according to an embodiment of the disclosure.

Referring to FIG. 25, a flowchart 2500 of an exemplary process for performing phototherapy inside a user's mouth using a phototherapeutic system (e.g., the phototherapeutic systems 100, 1400) is shown according to an embodiment of the disclosure. At step 2510, a phototherapeutic system is provided. The phototherapeutic system includes a housing, a plurality of radiation sources disposed in the housing, one or more sensors disposed in the housing, a user interface disposed on an exterior surface of the housing, a switch control circuit disposed in the housing, and one or more output components disposed in the housing. In an embodiment, the plurality of radiation sources is configured to provide to the user's mouth a plurality of beams. In an embodiment, at least two beams of the plurality of beams have different wavelengths. In an embodiment, a portion of the housing is configured to receive a pressure resulting from the user's mouth so as to prevent the housing from moving during the phototherapy. In an embodiment, the one or more sensors are configured to provide one or more values related to surrounding of the one or more sensors. In an embodiment, the user interface is configured to receive an input from the user for controlling operation of the phototherapeutic system.

At step 2520, an operating state of the phototherapeutic system is controlled, by the switch control circuit, based on the input received by the user interface and the one or more values provided by the one or more sensors. In an embodiment, the operating state of the phototherapeutic system is changed, by the switch control circuit, from a stop state to an active state when the input received by the user interface is indicative of the user's request to turn on the phototherapeutic system or start the phototherapy and the one or more values provided by the one or more sensors meet or cross the one or more respective thresholds. In an embodiment, the operating state of the phototherapeutic system is changed, by the switch control circuit, from the active state to the stop state when the one or more values provided by the one or more sensors do not all meet or cross the one or more respective thresholds during or after the phototherapy.

At step 2530, information related to the operating state of the phototherapeutic system is delivered by the one or more output components to the user. For example, when the operating state of the phototherapeutic system is changed from the stop state to the active state at step 2520, the information related to the state change is delivered by the one or more output components to the user. The one or more output components may include, but are not limited to, a display, a speaker, a flash-light emitter, or any combination thereof. For another example, upon receipt of the input from the user indicative of the user's request to turn on the phototherapeutic system or start the phototherapy, the operating state of the phototherapeutic system may still not be changed from the stop state to the active state when the one or more values provided by the one or more sensors do not all meet or cross the one or more respective thresholds. Accordingly, the information indicative of denying the user's request may be delivered to the user through the one or more output components.

Figure 26:
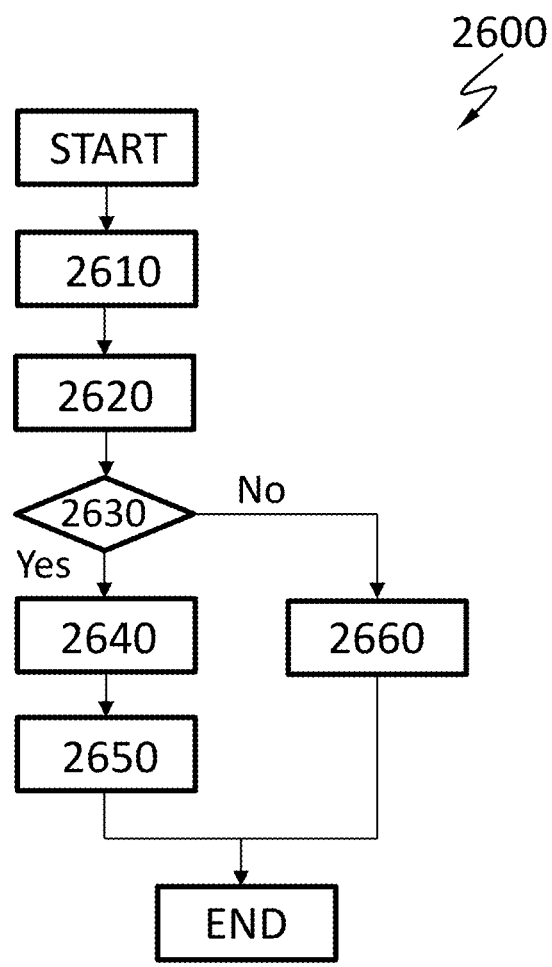
FIG. 26 is a flowchart of an exemplary process for performing phototherapy using a phototherapeutic system according to an embodiment of the disclosure.

Referring to FIG. 26, a flowchart 2600 of another exemplary process for performing phototherapy inside a user's mouth using a phototherapeutic system (e.g., the phototherapeutic systems 100, 1400) is shown according to an embodiment of the disclosure. At step 2610, a request to turn on the phototherapeutic system or start operating the phototherapeutic system is received from the user by a user interface. At step 2620, one or more values related to surroundings of one or more sensors of the phototherapeutic system are provided. The one or more sensors may include, but are not limited to, a photo-sensor, a temperature sensor, a distance sensor, and/or a pressure sensor. At step 2630, it is determined whether the values related to the surroundings of the one or more sensors satisfy a predetermined rule. In an embodiment, the predetermined rule is indicative that all the values related to the surroundings of the one or more sensors meet or cross respective thresholds. When it is determined at step 2630 that each of the one or more values related to the surroundings of the one or more sensors meets or crosses its respective threshold, the process proceeds to step 2640. At step 2640, a plurality of radiation beams is provided by a radiation generator of the phototherapeutic system inside the user's mouth. In an embodiment, at least two of the plurality of radiation beams have different wavelengths. In an embodiment, the radiation generator includes a plurality of radiation sources. The plurality of radiation sources may include, but is not limited to, LEDs, LDs, VECSELs, VCSELs, or any combination thereof. At step 2650, the plurality of radiation beams is modulated, by the radiation control circuit of the phototherapeutic system, according to one or more parameters selected from a group consisting of operating time period, average power, crest power, trough power, wave frequency, and/or wave shape. After step 2650 is complete, the process comes to an end. Further, when it is determined at step 2630 that at least one of the one or more values related to the surroundings of the one or more sensors does not meet or cross its respective threshold, the process proceeds to step 2660. At step 2660, information indicative of denying the user's request to operate the phototherapeutic system is delivered, by one or more output components, to the user responsive to the user's request to operate the phototherapeutic system. In an embodiment, the one or more output components may include, by are not limited to, a display, a speaker, a flash-light emitter, or any combination thereof. After step 2660 is complete, the process comes to the end.

In an embodiment, there is provided a phototherapeutic system for providing phototherapy inside a user's mouth, comprising: a housing; and a plurality of radiation sources disposed in the housing, wherein the plurality of radiation sources is configured to provide to the user's mouth a plurality of beams, wherein at least two beams of the plurality of beams have different wavelengths, and wherein a portion of the housing is configured to receive a pressure resulting from the user's mouth so as to prevent the housing from moving during the phototherapy.

In an embodiment, the portion of the housing is configured to provide a track for a mouth shield to be mounted on the housing and slide along the housing so as to adjust relative positions of the plurality of radiation sources with respect to the user's mouth, and wherein the mouth shield is configured to be bitten by the user so as to keep the user's mouth wide open during the phototherapy.

In an embodiment, the phototherapeutic system further comprises: one or more sensors disposed in the housing, wherein the one or more sensors are configured to provide one or more values related to surrounding of the one or more sensors, and wherein the one or more sensors comprise a photo sensor configured to provide a total intensity related to radiations from surrounding of the phototherapeutic system; a user interface disposed on an exterior surface of the housing, wherein the user interface is configured to receive an input for controlling operation of the phototherapeutic system; a switch control circuit disposed in the housing, wherein the switch control circuit is configured to control an operating state of the phototherapeutic system based on the input received by the user interface and the one or more values provided by the one or more sensors; and one or more output components disposed in the housing, the one or more output components being configured to deliver to the user information related to the operating state of the plurality of radiation sources.

In an embodiment, the switch control circuit is further configured to: change the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources; control the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and change the operating state of the phototherapeutic system, during operating of the phototherapeutic system, from the active state to the stop state when not all of the one or more values provided by the one or more sensors meet or cross the one or more respective thresholds.

In an embodiment, the first radiation source is configured to provide the first beam to the user's mouth, and the second radiation source is configured to provide the second beam to the user's mouth, a first portion of the first beam being not overlapped with a second portion of the second beam, and a second portion of the first beam being overlapped with a first portion of the second beam, and wherein the first radiation source is further configured to redirect the first beam until the first portion of the first beam is overlapped with the second portion of the second beam, the second portion of the first beam being not overlapped with the first portion of the second beam.

In an embodiment, the phototherapeutic system further comprises a radiation control circuit disposed in the housing and in communication with the switch control circuit, wherein the radiation control circuit is configured to modulate at least one of the plurality of beams with respect to one or more parameters selected from a group consisting of average power, crest power, trough power, wave frequency, wave shape, and operating time period based on the input received by the user interface.

In an embodiment, the phototherapeutic system further comprises a protection sleeve configured to cover the mouth shield, the housing, and the plurality of radiation sources so as to prevent the user from contaminating the mouth shield, the housing, and the plurality of radiation sources while allowing the plurality of beams provided by the plurality of radiation sources for passing through the protection sleeve.

In an embodiment, there is provided a method of providing phototherapy inside a user's mouth, comprising: providing a phototherapeutic system, comprising: a housing; a plurality of radiation sources disposed in the housing, wherein the plurality of radiation sources is configured to provide to the user's mouth a plurality of beams, wherein at least two beams of the plurality of beams have different wavelengths, wherein a portion of the housing is configured to receive a pressure resulting from the user's mouth so as to prevent the housing from moving during the phototherapy; one or more sensors disposed in the housing, wherein the one or more sensors are configured to provide one or more values related to surrounding of the one or more sensors; a user interface disposed on an exterior surface of the housing, wherein the user interface is configured to receive an input for controlling operation of the phototherapeutic system; a switch control circuit disposed in the housing; and one or more output components disposed in the housing; controlling, by the switch control circuit, an operating state of the phototherapeutic system based on the input received by the user interface and the one or more values provided by the one or more sensors; and delivering, by the one or more output components, to the user information related to the operating state of the phototherapeutic system.

In an embodiment, the method further comprises: changing the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources; controlling the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and changing the operating state of the phototherapeutic system, during operating of the phototherapeutic system, from the active state to the stop state when not all of the one or more values provided by the one or more sensors meet or cross the one or more respective thresholds.

In an embodiment, a first beam of the at least two beams provided by a first radiation source has a wavelength between 500 nanometers (nm) and 700 nm, and a second beam of the at least two beams provided by a second radiation source has a wavelength between 700 nm and 900 nm, and wherein the one or more sensors comprise a photo sensor configured to provide a total intensity related to radiations from surrounding of the photo sensor.

In an embodiment, both the first beam and the second beam have a beam angle between 25 degrees and 30 degrees, wherein the first beam is overlapped with the second beam in the user's mouth, wherein a first irradiation spot in the user's mouth resulting from the first beam has a first diameter between 2 cm and 5 cm, and a second irradiation spot in the user's mouth resulting from the second beam has a second diameter between 2 cm and 5 cm, and wherein an overlapped portion between the first irradiation spot and the second irradiation spot has a third diameter between 1 cm and 3.5 cm.

In an embodiment, the method further comprises: providing, by the first radiation source and the second radiation source respectively, the first beam and the second beam to the user's mouth, a first portion of the first beam being not overlapped with a second portion of the second beam, and a second portion of the first beam being overlapped with a first portion of the second beam; and redirecting, by the first radiation source, the first beam until the first portion of the first beam is overlapped with the second portion of the second beam, the second portion of the first beam being not overlapped with the first portion of the second beam.

In an embodiment, the phototherapeutic system further comprises a radiation control circuit disposed in the housing and in communication with the switch control circuit, and wherein the method further comprises modulating, by the radiation control circuit, at least one of the plurality of beams with respect to one or more parameters selected from a group consisting of average power, crest power, trough power, wave frequency, wave shape, and operating time period based on the input received by the user interface.

In an embodiment, each of the plurality of beams has a power between 5 mW and 20 mW, and wherein the plurality of radiation sources comprises one or more radiation sources selected from a group consisting of LEDs, LDs, VECSELs, and VCSELs.

In an embodiment, there is provided a machine-readable tangible and non-transitory medium having instructions for providing phototherapy inside a user's mouth through a phototherapeutic system, the phototherapeutic system comprising: a housing; a plurality of radiation sources disposed in the housing, wherein the plurality of radiation sources is configured to provide to the user's mouth a plurality of beams, wherein at least two beams of the plurality of beams have different wavelengths, wherein a portion of the housing is configured to receive a pressure resulting from the user's mouth so as to prevent the housing from moving during the phototherapy; one or more sensors disposed in the housing, wherein the one or more sensors are configured to provide one or more values related to surrounding of the one or more sensors; a user interface disposed on an exterior surface of the housing, wherein the user interface is configured to receive an input for controlling operation of the phototherapeutic system; a switch control circuit disposed in the housing; and one or more output components disposed in the housing, wherein the instructions, when read by a hardware processor system, causes the hardware processor system to: control, through the switch control circuit, an operating state of the phototherapeutic system based on the input received by the user interface and the one or more values provided by the one or more sensors; and deliver, through the one or more output components, to the user information related to the operating state of the phototherapeutic system.

In an embodiment, the machine-readable tangible and non-transitory medium of claim 15, wherein the instructions, when read by the hardware processor system, further causes the hardware processor system to: change the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources; control the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and change the operating state of the phototherapeutic system, during operating of the phototherapeutic system, from the active state to the stop state when not all of the one or more values provided by the one or more sensors meet or cross the one or more respective thresholds.

In an embodiment, a first beam of the at least two beams provided by a first radiation source has a wavelength between 500 nm and 700 nm, and a second beam of the at least two beams provided by a second radiation source has a wavelength between 700 nm and 900 nm, and wherein the one or more sensors comprise a photo sensor configured to provide a total intensity related to radiations from surrounding of the photo sensor.

In an embodiment, both the first beam and the second beam have a beam angle between 25 degrees and 30 degrees, wherein the first beam is overlapped with the second beam in the user's mouth, wherein a first irradiation spot in the user's mouth resulting from the first beam has a first diameter between 2 cm and 5 cm, and a second irradiation spot in the user's mouth resulting from the second beam has a second diameter between 2 cm and 5 cm, and wherein an overlapped portion between the first irradiation spot and the second irradiation spot has a third diameter between 1 cm and 3.5 cm.

In an embodiment, the instructions, when read by the hardware processor system, further causes the hardware processor system to: provide, through the first radiation source and the second radiation source respectively, the first beam and the second beam to the user's mouth, a first portion of the first beam being not overlapped with a second portion of the second beam, and a second portion of the first beam being overlapped with a first portion of the second beam; and redirect, through the first radiation source, the first beam until the first portion of the first beam is overlapped with the second portion of the second beam, the second portion of the first beam being not overlapped with the first portion of the second beam.

In an embodiment, the phototherapeutic system further comprises a radiation control circuit disposed in the housing and in communication with the switch control circuit, and wherein the instructions, when read by the hardware processor system, further causes the hardware processor system to modulate, through the radiation control circuit, at least one of the plurality of beams with respect to one or more parameters selected from a group consisting of average power, crest power, trough power, wave frequency, wave shape, and operating time period based on the input received by the user interface.

Those skilled in the art will recognize that the present disclosure is amenable to a variety of modifications and/or enhancements. For example, although the implementation of various components described above may be embodied in a hardware device, it can also be implemented as a firmware, firmware/software combination, firmware/hardware combination, or a hardware/firmware/software combination.

While the foregoing description and drawings represent embodiments of the present disclosure, it will be understood that various additions, modifications, and substitutions may be made therein without departing from the spirit and scope of the principles of the present disclosure as defined in the accompanying claims. One skilled in the art will appreciate that the present disclosure may be used with many modifications of form, structure, arrangement, proportions, materials, elements, and components and otherwise, used in the practice of the disclosure, which are particularly adapted to specific environments and operative requirements without departing from the principles of the present disclosure. The presently disclosed embodiments are therefore to be considered in all respects as illustrative and not restrictive, the scope of the present disclosure being indicated by the appended claims and their legal equivalents, and not limited to the foregoing description.

What is claimed is:

1. A phototherapeutic system for providing phototherapy inside a user's mouth, comprising:
   a housing; and
   a plurality of radiation sources disposed in the housing, wherein the plurality of radiation sources is configured to provide to the user's mouth a plurality of beams, wherein at least two beams of the plurality of beams have different wavelengths, wherein a portion of the housing is configured to receive a pressure resulting from the user's mouth so as to prevent the housing from moving during the phototherapy, and wherein the portion of the housing comprises a saw-tooth shaped track, the saw-tooth shaped track being configured to allow the user to apply pressure on the portion of the housing by biting between adjacent teeth of the saw-tooth shaped track, and the saw-tooth shaped track being further configured to allow a mouth shield to be mounted on the housing, the mouth shield being configured to:
  slide back and forth along the housing so as to adjust positions of the plurality of radiation sources inside the user's mouth; and
  prevent, by allowing the user to bite the mouth shield, the phototherapeutic system from slipping into the user's digestive canal or being swallowed by the user when the mouth shield is mounted on the housing during operation of the phototherapeutic system.

2. The phototherapeutic system of claim 1, wherein each period of a beam waveform has a combination of different wave shapes selected from a group consisting of a rectangle, a triangle, a sinusoidal shape, a square, and a semi-circle, and wherein at least one of the plurality of radiation sources is configured to rotate at its own location so that radiation beams provided by the at least one of the radiation sources are redirected to different directions at different times.

3. The phototherapeutic system of claim 2, wherein the plurality of radiation sources comprise a first radiation source and a second radiation source, wherein the first radiation source is configured to provide a first beam to the user's mouth, and the second radiation source is configured to provide a second beam to the user's mouth, a first portion of the first beam being not overlapped with a second portion of the second beam, and a second portion of the first beam being overlapped with a first portion of the second beam, and wherein the first radiation source is further configured to redirect the first beam until the first portion of the first beam is overlapped with the second portion of the second beam, the second portion of the first beam being not overlapped with the first portion of the second beam.

4. The phototherapeutic system of claim 1, further comprising:
  one or more sensors disposed in the housing, wherein the one or more sensors are configured to provide one or more values related to surrounding of the one or more sensors, and wherein the one or more sensors comprise a photo sensor configured to provide a total intensity related to radiations from surrounding of the phototherapeutic system;
  a user interface disposed on an exterior surface of the housing, wherein the user interface is configured to receive an input for controlling operation of the phototherapeutic system;
  a switch control circuit disposed in the housing, wherein the switch control circuit is configured to control an operating state of the phototherapeutic system based on the input received by the user interface and the one or more values provided by the one or more sensors; and
  one or more output components disposed in the housing, the one or more output components being configured to deliver to the user information related to the operating state of the plurality of radiation sources.

5. The phototherapeutic system of claim 4, wherein the switch control circuit is further configured to:

change the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources;

control the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and change the operating state of the phototherapeutic system, during operating of the phototherapeutic system, from the active state to the stop state when not all of the one or more values provided by the one or more sensors meet or cross the one or more respective thresholds.

6. The phototherapeutic system of claim 5, further comprising a radiation control circuit disposed in the housing and in communication with the switch control circuit, wherein the radiation control circuit is configured to modulate at least one of the plurality of beams with respect to one or more parameters selected from a group consisting of average power, crest power, trough power, wave frequency, wave shape, and operating time period based on the input received by the user interface.

7. The phototherapeutic system of claim 6, further comprising a protection sleeve configured to cover the mouth shield, the housing, and the plurality of radiation sources so as to prevent the user from contaminating the mouth shield, the housing, and the plurality of radiation sources while allowing the plurality of beams provided by the plurality of radiation sources for passing through the protection sleeve.

8. A method of providing phototherapy inside a user's mouth, comprising:
  providing a phototherapeutic system, comprising:
    a housing;
    a plurality of radiation sources disposed in the housing, wherein the plurality of radiation sources is configured to provide to the user's mouth a plurality of beams, wherein at least two beams of the plurality of beams have different wavelengths, wherein at least one of the plurality of radiation sources is configured to rotate at its own location so that radiation beams provided by the at least one of the radiation sources are redirected to different directions at different times, wherein a portion of the housing is configured to receive a pressure resulting from the user's mouth so as to prevent the housing from moving during the phototherapy, and wherein the portion of the housing comprises a saw-tooth shaped track,
    the saw-tooth shaped track being configured to allow the user to apply pressure on the portion of the housing by biting between adjacent teeth of the saw-tooth shaped track, and
    the saw-tooth shaped track being further configured to allow a mouth shield to be mounted on the housing, the mouth shield being configured to:
      slide back and forth along the housing so as to adjust positions of the plurality of radiation sources inside the user's mouth; and
      prevent, by allowing the user to bite the mouth shield, the phototherapeutic system from slipping into the user's digestive canal or being swallowed by the user when the mouth shield is mounted on the housing during operation of the phototherapeutic system,
one or more sensors disposed in the housing, wherein the one or more sensors are configured to provide one or more values related to surrounding of the one or more sensors;
a user interface disposed on an exterior surface of the housing, wherein the user interface is configured to receive an input for controlling operation of the phototherapeutic system;
a switch control circuit disposed in the housing; and
one or more output components disposed in the housing;
controlling, by the switch control circuit, an operating state of the phototherapeutic system based on the input received by the user interface and the one or more values provided by the one or more sensors; and
delivering, by the one or more output components, to the user information related to the operating state of the phototherapeutic system.

9. The method of claim 8, wherein each period of a beam waveform has a combination of different wave shapes selected from a group consisting of a rectangle, a triangle, a sinusoidal shape, a square, and a semi-circle, the method further comprising:
changing the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources;
controlling the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and
changing the operating state of the phototherapeutic system, during operating of the phototherapeutic system, from the active state to the stop state when not all of the one or more values provided by the one or more sensors meet or cross the one or more respective thresholds.

10. The method of claim 9, wherein a first beam of the at least two beams provided by a first radiation source has a wavelength between 500 nanometers (nm) and 700 nm, and a second beam of the at least two beams provided by a second radiation source has a wavelength between 700 nm and 900 nm, and wherein the one or more sensors comprise a photo sensor configured to provide a total intensity related to radiations from surrounding of the photo sensor.

11. The method of claim 10, wherein both the first beam and the second beam have a beam angle between 25 degrees and 30 degrees, wherein the first beam is overlapped with the second beam in the user's mouth, wherein a first irradiation spot in the user's mouth resulting from the first beam has a first diameter between 2 centimeters (cm) and 5 cm, and a second irradiation spot in the user's mouth resulting from the second beam has a second diameter between 2 cm and 5 cm, and wherein an overlapped portion between the first irradiation spot and the second irradiation spot has a third diameter between 1 cm and 3.5 cm.

12. The method of claim 11, further comprising:
providing, by the first radiation source and the second radiation source respectively, the first beam and the second beam to the user's mouth, a first portion of the first beam being not overlapped with a second portion of the second beam, and a second portion of the first beam being overlapped with a first portion of the second beam; and
redirecting, by the first radiation source, the first beam until the first portion of the first beam is overlapped with the second portion of the second beam, the second portion of the first beam being not overlapped with the first portion of the second beam.

13. The method of claim 11, wherein the phototherapeutic system further comprises a radiation control circuit disposed in the housing and in communication with the switch control circuit, and wherein the method further comprises modulating, by the radiation control circuit, at least one of the plurality of beams with respect to one or more parameters selected from a group consisting of average power, crest power, trough power, wave frequency, wave shape, and operating time period based on the input received by the user interface.

14. The method of claim 13, wherein each of the plurality of beams has a power between 5 milliwatts (mW) and 20 mW, and wherein the plurality of radiation sources comprises one or more radiation sources selected from a group consisting of light-emitting diodes (LEDs), laser diodes (LDs), vertical external cavity surface emitting lasers (VECSELs), and vertical cavity surface emitting lasers (VCSELs).

15. A machine-readable tangible and non-transitory medium having instructions for providing phototherapy inside a user's mouth through a phototherapeutic system, the phototherapeutic system comprising:
a housing;
a plurality of radiation sources disposed in the housing, wherein the plurality of radiation sources is configured to provide to the user's mouth a plurality of beams, wherein at least two beams of the plurality of beams have different wavelengths, wherein at least one of the plurality of radiation sources is configured to rotate at its own location so that radiation beams provided by the at least one of the radiation sources are redirected to different directions at different times, and wherein a portion of the housing is configured to receive a pressure resulting from the user's mouth so as to prevent the housing from moving during the phototherapy, and wherein the portion of the housing comprises a saw-tooth shaped track,
the saw-tooth shaped track being configured to allow the user to apply pressure on the portion of the housing by biting between adjacent teeth of the saw-tooth shaped track, and
the saw-tooth shaped track being further configured to allow a mouth shield to be mounted on the housing, the mouth shield being configured to:
slide back and forth along the housing so as to adjust positions of the plurality of radiation sources inside the user's mouth; and
prevent, by allowing the user to bite the mouth shield, the phototherapeutic system from slipping into the user's digestive canal or being swallowed by the user when the mouth shield is mounted on the housing during operation of the phototherapeutic system,
one or more sensors disposed in the housing, wherein the one or more sensors are configured to provide one or more values related to surrounding of the one or more sensors;

a user interface disposed on an exterior surface of the housing, wherein the user interface is configured to receive an input for controlling operation of the phototherapeutic system;

a switch control circuit disposed in the housing; and one or more output components disposed in the housing, wherein the instructions, when read by a hardware processor system, causes the hardware processor system to:

control, through the switch control circuit, an operating state of the phototherapeutic system based on the input received by the user interface and the one or more values provided by the one or more sensors; and deliver, through the one or more output components, to the user information related to the operating state of the phototherapeutic system.

16. The machine-readable tangible and non-transitory medium of claim 15, wherein each period of a beam waveform has a combination of different wave shapes selected from a group consisting of a rectangle, a triangle, a sinusoidal shape, a square, and a semi-circle, and wherein the instructions, when read by the hardware processor system, further causes the hardware processor system to:

change the operating state of the phototherapeutic system from a stop state to an active state responsive to a user's request to operate the phototherapeutic system and the one or more values provided by the one or more sensors meeting or crossing one or more respective thresholds, wherein, in the active state, the plurality of beams is provided by the plurality of radiation sources, and wherein, in the stop state, the plurality of beams is not provided by the plurality of radiation sources;

control the one or more output components to deliver to the user the information indicative of denying the user's request to operate the phototherapeutic system responsive to the user's request to operate the phototherapeutic system when not all of the one or more values provided by the one or more sensors meet or cross the one or more respective thresholds; and change the operating state of the phototherapeutic system, during operating of the phototherapeutic system, from the active state to the stop state when not all of the one or more values provided by the one or more sensors meet or cross the one or more respective thresholds.

17. The machine-readable tangible and non-transitory medium of claim 16, wherein a first beam of the at least two beams provided by a first radiation source has a wavelength between 500 nanometers (nm) and 700 nm, and a second beam of the at least two beams provided by a second radiation source has a wavelength between 700 nm and 900 nm, and wherein the one or more sensors comprise a photo sensor configured to provide a total intensity related to radiations from surrounding of the photo sensor.

18. The machine-readable tangible and non-transitory medium of claim 17, wherein both the first beam and the second beam have a beam angle between 25 degrees and 30 degrees, wherein the first beam is overlapped with the second beam in the user's mouth, wherein a first irradiation spot in the user's mouth resulting from the first beam has a first diameter between 2 centimeters (cm) and 5 cm, and a second irradiation spot in the user's mouth resulting from the second beam has a second diameter between 2 cm and 5 cm, and wherein an overlapped portion between the first irradiation spot and the second irradiation spot has a third diameter between 1 cm and 3.5 cm.

19. The machine-readable tangible and non-transitory medium of claim 18, wherein the instructions, when read by the hardware processor system, further causes the hardware processor system to:

provide, through the first radiation source and the second radiation source respectively, the first beam and the second beam to the user's mouth, a first portion of the first beam being not overlapped with a second portion of the second beam, and a second portion of the first beam being overlapped with a first portion of the second beam; and redirect, through the first radiation source, the first beam until the first portion of the first beam is overlapped with the second portion of the second beam, the second portion of the first beam being not overlapped with the first portion of the second beam.

20. The machine-readable tangible and non-transitory medium of claim 19, wherein the phototherapeutic system further comprises a radiation control circuit disposed in the housing and in communication with the switch control circuit, and wherein the instructions, when read by the hardware processor system, further causes the hardware processor system to modulate, through the radiation control circuit, at least one of the plurality of beams with respect to one or more parameters selected from a group consisting of average power, crest power, trough power, wave frequency, wave shape, and operating time period based on the input received by the user interface.

* * * * *